(12) United States Patent
Guerrero-Preston et al.

(10) Patent No.: US 9,328,379 B2
(45) Date of Patent: May 3, 2016

(54) HYPERMETHYLATION BIOMARKERS FOR DETECTION OF HEAD AND NECK SQUAMOUS CELL CANCER

(75) Inventors: Rafael Enrique Guerrero-Preston, Baltimore, MD (US); David Sidransky, Baltimore, MD (US); Ethan Soudry, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 13/634,321

(22) PCT Filed: Mar. 11, 2011

(86) PCT No.: PCT/US2011/028011
§ 371 (c)(1),
(2), (4) Date: Nov. 26, 2012

(87) PCT Pub. No.: WO2011/112880
PCT Pub. Date: Sep. 15, 2011

(65) Prior Publication Data
US 2013/0071842 A1 Mar. 21, 2013

Related U.S. Application Data

(60) Provisional application No. 61/313,383, filed on Mar. 12, 2010.

(51) Int. Cl.
*C12Q 1/68* (2006.01)
*C12P 19/34* (2006.01)

(52) U.S. Cl.
CPC .............. *C12Q 1/686* (2013.01); *C12Q 1/6886* (2013.01); *C12Q 2600/154* (2013.01); *C12Q 2600/158* (2013.01)

(58) Field of Classification Search
CPC ........... C12Q 2600/158; C12Q 1/6886; C12Q 1/6883; C12Q 2600/112; C12Q 1/6806; C12Q 2600/106; C12Q 2600/142; C12Q 1/6869; C12Q 2523/125; C12Q 2563/161; C12Q 2600/118; C12Q 2600/154; C12Q 1/6827; C12Q 1/6858; C12Q 2600/156; C12Q 2521/331; C12Q 2525/119; C12Q 2537/164; C12Q 2549/119; C12Q 2563/159; C12Q 1/686
See application file for complete search history.

(56) References Cited

U.S. PATENT DOCUMENTS

2009/0005258 A1* 1/2009 Holstege et al. ................. 506/9
2010/0280134 A1* 11/2010 Renard et al. ................ 514/789

OTHER PUBLICATIONS

Tan et al. British Journal of Cancer 2008 vol. 99 pp. 357-363.*
Michels et al. Experimental Gerontology 2010 vol. 45 pp. 297-301.*
Feng et al. PNAS 2010 vol. 107 No. 19 pp. 8689-8694.*
Lleras et al. Clin Cancer Res 2013 vol. 19 pp. 5444-5455 Pub online Jul. 26, 2013.*
Duffy et al. European Journal of Cancer 2009 pp. 335-346.*
Glazer, C., et al., "Applying the molecular biology and epigenetics of head and neck cancer in everyday clinical practice", Oral Oncol, 2009. 45(4-5): p. 440-6.
Kagan, J., et al., "Towards Clinical Application of Methylated DNA Sequences as Cancer Biomarkers: A Joint NCI's EDRN and NIST Workshop on Standards, Methods, Assays, Reagents and Tools", Cancer Res. May 15, 2007, 67(10): p. 4545-9.
Hudson, T., et al., "International network of cancer genome projects", Nature, Apr. 15, 2010, 464(7291): p. 993-8.
Ha, P., et al., "Promoter methylation and inactivation of tumour-suppressor genes in oral squamous-cell carcinoma", Lancet Oncol, Jan. 2006. 7(1): p. 77-82.
Smith, I., et al., "Coordinated activation of candidate proto-oncogenes and cancer testes antigens via promoter demethylation in head and neck cancer and lung cancer", PLoS One, Mar. 2009. 4(3): p. e4961.
Glazer, C., et al., "Integrative discovery of epigenetically derepressed cancer testis antigens in NSCLC", PLoS One, 2009. 4(12): p. c8189.
Rosas, S., et al., "Promoter hypermethylation patterns of p16, O6-methylguanine-DNA-methyltransferase and death associated protein kinase in tumors and saliva of head and neck cancer patients", Cancer Res, (2001) 61(3): p. 939-42.
Shaw, R., "The epigenetics of oral cancer", Int J Ortl Maxillofac Surg, 2006. 35(2); p. 101-8.
Carvalho, A., et al., "Evaluation of promoter hypermethylation detection in body fluids as a screening/diagnosis tool for head and neck squamous cell carcinoma", Clin Cancer Res, Jan. 1, 2008, 14(1): p. 97-107.
Chang, X., et al., "Identification of hypermethylated genes associated with cisplatin resistance in human cancers", Cancer Res., Apr. 1, 2010, 70(7): p. 2870-9.
Demokan, S., et al., "KIFIA and EDNRB are differentially methylated in primary HNSCC and salivary rinses", Int J Cancer, (2010) 127(10): p. 2351-9.

(Continued)

*Primary Examiner* — Jehanne Sitton
(74) *Attorney, Agent, or Firm* — John Hopkins Technology Transfer

(57) ABSTRACT

Differentially methylated oral squamous cell carcinoma (OSCC) biomarkers, identified in-vitro and validated in well-characterized surgical specimens, have shown poor clinical correlation in cohorts with different risk profiles. To overcome this lack of relevance we used the HumanMethylation27 BeadChip, publicly available methylation and expression array data, and Quantitative Methylation Specific PCR to uncover differential methylation in OSCC clinical samples with heterogeneous risk profiles. A two stage-design consisting of Discovery and Prevalence screens was used to identify differential promoter methylation and deregulated pathways in patients diagnosed with OSCC and head and neck squamous cell carcinoma. This Phase I Biomarker Development Trial identified a panel of differentially methylated genes in normal and OSCC clinical samples from patients with heterogeneous risk profiles. This panel may be useful for early detection and cancer prevention studies.

7 Claims, 7 Drawing Sheets

(56) References Cited

OTHER PUBLICATIONS

Pattani, K.M., et al., "Endothelin receptor type B gene promoter hypermethylation in salivary rinses is independently associated with risk of oral cavity cancer and premalignancy", Cancer Prev Res (2010). 3(9): p. 1093-103.
Righini, C.A., et al., "Tumor-specific methylation in saliva: a promising biomarker for early detection of head and neck cancer recurrence", Clin Cancer Res. (2007) 13(4): p. 1179-85.
Viet, C.T., et al., "Methylation array analysis of preoperative and postoperative saliva DNA in oral cancer patients", Cancer Epidemiol Biomarkers Prev,. Dec. 2008. 17(12): p. 3603-11.
Yamashita, K., et al., Genetics supersedes epigenetics in colon cancer phenotype. Cancer Cell. Aug. 2003, 4(2): p. 121-31.
Marsit, C.J., et al., "Epigenetic profiling reveals etiologically distinct patterns of DNA methylation in head and neck squamous cell carcinoma", Carcinogenesis, (2009) 30(3): p. 416-22.
Smith, I.M., et al., "DNA global hypomethylation in squamous cell head and neck cancer associated with smoking, alcohol consumption and stage", Int J Cancer, (2007) 121(8): p. 1724-8.
Hawkins, R.D., et al., Next-generation genomics: an integrative approach. Nat Rev Genet. (2010), 11(7): p. 476-486.
Hawkins, R.D., et al., "Distinct epigenomic landscapes of pluripotent and lineage-committed human cells", Cell Stem Cell, May 7, 2010, 6(5): p. 479-91.
Pepe, M. S., et al., "Phases of biomarker development for early detection of cancer", J Natl Cancer Inst. Jul. 18, 2001, 93(14): p. 1054-61.
Srivastava, S., "Cancer biomarker discovery and development in gastrointestinal cancers: early detection research network-a collaborative approach", Gastroinest Cancer Res, (2007) 1(4Suppl2): p. S60-3.

Fang YC, et al., "MeInfoText: associated gene methylation and cancer information from text mining", BMC Bioinformatics, (2008), 9:22.
He, X, et al., "MethylCancer: the database human DNA methylation and cancer", Nucleic Acids Res, (2008), 36 (Database issue): p. D836-41.
Sticht, C., et al., "Activation MAP kinase signaling through ERK5 but not ERKI expression is associated with lymph node metastases in oral squamous cell carcinoma (OSCC)", Neoplasia, May 2008 10(5): p. 462-70.
Hoque, M.O., et al., "Quantification of promoter methylation of multiple genes in urine DNA and bladder cancer detection", J Natl Cancer Inst, (2006) 98(14): p. 996-1004.
Ulazzi, L., et al., "Nidogen 1 and 2 gene promoters are aberrantly methylated in human gastrointestinal cancer" Mol Cancer, (2007). 6: p. 17.
Carvalho, A.L., et al., "Deleted in colorectal cancer is a putative conditional tumor-suppressor gene inactivated by promoter hypermethylation in head and neck squamous cell carcinoma", Cancer Research, Oct. 1, 2006, 66(19) pp. 9401-9407.
Hasegawa, M., et al., "Patterns of gene promoter methylation in squamous cell cancer of head and neck", Oncogene, Jun. 20, 2002, vol. 21(27), pp. 4231-4236.
Loyo, M., et al., "A survey of methylated candidate tumor suppressor genes in nasopharyngeal carconoma", International Journal of Cancer, Mar. 15, 2011, vol. 128(6), pp. 1393-1403.
Guerrero-Preston, R., et al., "NID2 and HOXA0 promoter hypermethylation as biomarkers for prevention and early detection in oral cavity squamous cell carcinoma tissues and saliva", Cancer Prevention Research, May 10, 2011, vol. 4(7), pp. 1061-1072.

\* cited by examiner

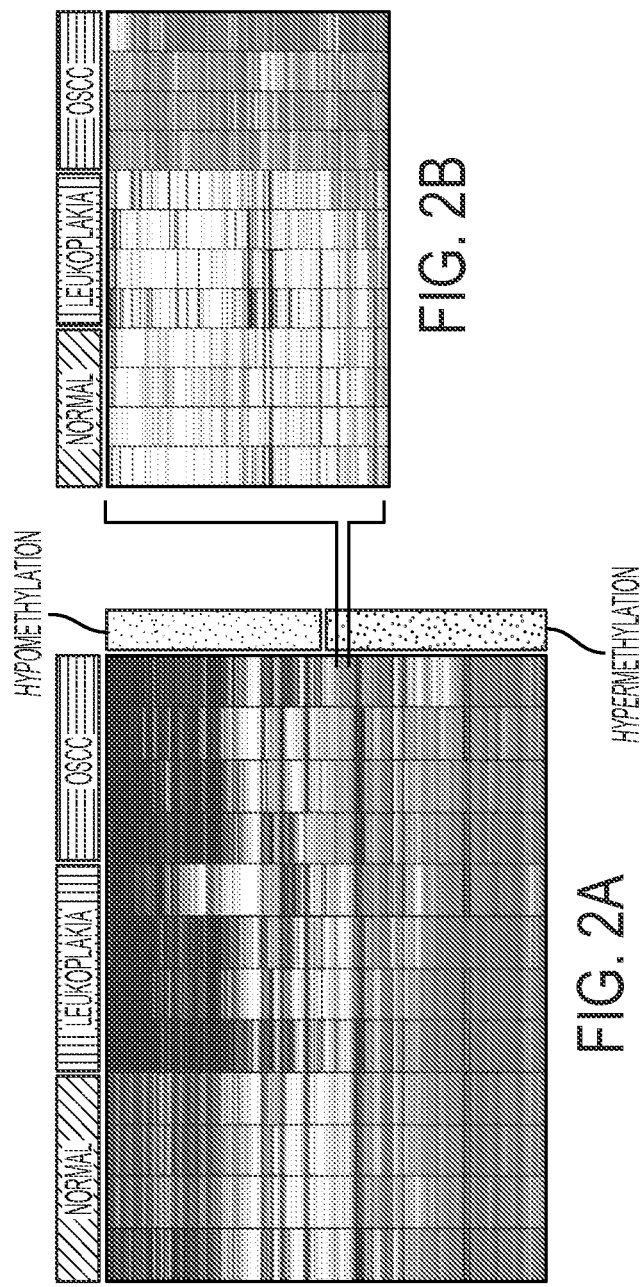

MSP PRIMERS AND PROBES

| GENE | FORWARD 5'-3' | PROBE 6FAM 5'-3' TAMRA | REVERSE 5'-3' |
|---|---|---|---|
| ACTB | TGG TGA TGG AGG AGG TTT AGT AAG T | ACC ACC ACC CAA CAC ACA ATA ACA AAC ACA | AAC CAA TAA AAC CTA CTC CTC CCT TAA |
| DCC | CGGCGATTTTGGTTTCGAAGG | GGTTTTTGTATTTTCGGAGTTTTTTG | TACCGATTACTTAAAAATACGCG |
| KIF1A | GCGCGGATAAATTAGTTGGCGATT | CCT CCC GAA ACG CTA ATT AAC TAC GCG | CTC GAC GAC TAC TCT ACG CTA T |
| NID2 | GCGGGTTTTTAAGGAGTTTTATTTTC | ACGCGCTACCCCAAACCTTACCGA | CTACGAAATTCCCTTTACGCT |
| HOXA9 | AATAAATTTATCGTAGAGGGGTAC | GGGCCCCCATTAACCGTACGCGT | CATATACAACTTAATAACACCGAA |
| MCAM | AGAAATTTAGTTCGGTTTTTATCG | ACAATATCAAACGGAGACAACGAC | ACGCAAAATTCTTCTCCCAAAA |
| CALCA | GTTTTGGAAGTATGAGGGTGACG | ATTCCGCCAATACACACAACCAATAAAC G | TTCCCGCCGCTATAAATCG |
| GATA4 | GTTAGTTAGCCGTTTTAGGGTCCA | CCAACTCGCGGACTCGAATCCCCGA | ACGACGACGAAACCTCTCG |
| EDNRB | GGG AGT AGT TGT AGT TTA GTT AGT TAG GGA GTA G | TTT TTA TTC GTC GGG AGG AG | CCC GCG ATT AAA CTC GAA AA |

FIG. 6

SEQUENCE LISTING

```
<160> NUMBER OF SEQ ID NOS: 27

<210> SEQ ID NO 1
<211> LENGTH: 25
<212> TYPE: DNA
<213> ORGANISM: Artificial Sequence
<220> FEATURE:
<223> OTHER INFORMATION: probes and primers for amplification

<400> SEQUENCE: 1
tggtgatgga ggaggtttag taagt                                           25

<210> SEQ ID NO 2
<211> LENGTH: 30
<212> TYPE: DNA
<213> ORGANISM: Artificial Sequence
<220> FEATURE:
<223> OTHER INFORMATION: probes and primers for amplification

<400> SEQUENCE: 2
accaccaccc aacacacaat aacaaacaca                                      30

<210> SEQ ID NO 3
<211> LENGTH: 27
<212> TYPE: DNA
<213> ORGANISM: Artificial Sequence
<220> FEATURE:
<223> OTHER INFORMATION: probes and primers for amplification

<400> SEQUENCE: 3
aaccaataaa acctactcct cccttaa                                         27

<210> SEQ ID NO 4
<211> LENGTH: 21
<212> TYPE: DNA
<213> ORGANISM: Artificial Sequence
<220> FEATURE:
<223> OTHER INFORMATION: probes and primers for amplification

<400> SEQUENCE: 4
```
cgcgattttt ggtttcgaag g                                         21

<210> SEQ ID NO 5
<211> LENGTH: 28
<212> TYPE: DNA
<213> ORGANISM: Artificial Sequence
<220> FEATURE:
<223> OTHER INFORMATION: probes and primers for amplification

<400> SEQUENCE: 5
ggtttttgta tttttcggag tttttttg                                  28

<210> SEQ ID NO 6
<211> LENGTH: 23
<212> TYPE: DNA
<213> ORGANISM: Artificial Sequence
<220> FEATURE:
<223> OTHER INFORMATION: probes and primers for amplification

<400> SEQUENCE: 6
taccgattac ttaaaaatac gcg                                       23

<210> SEQ ID NO 7
<211> LENGTH: 23
<212> TYPE: DNA
<213> ORGANISM: Artificial Sequence
<220> FEATURE:
<223> OTHER INFORMATION: probes and primers for amplification

<400> SEQUENCE: 7
gcgcgataaa ttagttggcg att                                       23

<210> SEQ ID NO 8
<211> LENGTH: 27
<212> TYPE: DNA
<213> ORGANISM: Artificial Sequence
<220> FEATURE:
<223> OTHER INFORMATION: probes and primers for amplification

<400> SEQUENCE: 8
cctcccgaaa cgctaattaa ctacgcg                                   27

<210> SEQ ID NO 9
<211> LENGTH: 22
<212> TYPE: DNA
<213> ORGANISM: Artificial Sequence
<220> FEATURE:
<223> OTHER INFORMATION: probes and primers for amplification

<400> SEQUENCE: 9
ctcgacgact actctacgct at                                        22

<210> SEQ ID NO 10
<211> LENGTH: 25
<212> TYPE: DNA
<213> ORGANISM: Artificial Sequence
<220> FEATURE:
<223> OTHER INFORMATION: probes and primers for amplification

<400> SEQUENCE: 10
gcggttttta aggagtttta ttttc                                     25

<210> SEQ ID NO 11
<211> LENGTH: 24
<212> TYPE: DNA
<213> ORGANISM: Artificial Sequence

```
<220> FEATURE:
<223> OTHER INFORMATION: probes and primers for amplification

<400> SEQUENCE: 11
acgccgctac cccaaacctt acga                                              24

<210> SEQ ID NO 12
<211> LENGTH: 21
<212> TYPE: DNA
<213> ORGANISM: Artificial Sequence
<220> FEATURE:
<223> OTHER INFORMATION: probes and primers for amplification

<400> SEQUENCE: 12
ctacgaaatt ccctttacgc t                                                 21

<210> SEQ ID NO 13
<211> LENGTH: 25
<212> TYPE: DNA
<213> ORGANISM: Artificial Sequence
<220> FEATURE:
<223> OTHER INFORMATION: probes and primers for amplification

<400> SEQUENCE: 13
aataaatttt atcgtagagc ggtac                                             25

<210> SEQ ID NO 14
<211> LENGTH: 23
<212> TYPE: DNA
<213> ORGANISM: Artificial Sequence
<220> FEATURE:
<223> OTHER INFORMATION: probes and primers for amplification

<400> SEQUENCE: 14
gcgcccccat taaccgtacg cgt                                               23

<210> SEQ ID NO 15
<211> LENGTH: 25
<212> TYPE: DNA
<213> ORGANISM: Artificial Sequence
<220> FEATURE:
<223> OTHER INFORMATION: probes and primers for amplification

<400> SEQUENCE: 15
catataacaa cttaataaca ccgaa                                             25

<210> SEQ ID NO 16
<211> LENGTH: 23
<212> TYPE: DNA
<213> ORGANISM: Artificial Sequence
<220> FEATURE:
<223> OTHER INFORMATION: probes and primers for amplification

<400> SEQUENCE: 16
agaatttagg tcggttttta tcg                                               23

<210> SEQ ID NO 17
<211> LENGTH: 25
<212> TYPE: DNA
<213> ORGANISM: Artificial Sequence
<220> FEATURE:
<223> OTHER INFORMATION: probes and primers for amplification

<400> SEQUENCE: 17
acaatatcaa accgacgaca acgac                                             25
```

```
<210> SEQ ID NO 18
<211> LENGTH: 22
<212> TYPE: DNA
<213> ORGANISM: Artificial Sequence
<220> FEATURE:
<223> OTHER INFORMATION: probes and primers for amplification

<400> SEQUENCE: 18
acgcaaaatt cttctcccaa aa                                              22

<210> SEQ ID NO 19
<211> LENGTH: 23
<212> TYPE: DNA
<213> ORGANISM: Artificial Sequence
<220> FEATURE:
<223> OTHER INFORMATION: probes and primers for amplification

<400> SEQUENCE: 19
gttttggaag tatgagggtg acg                                             23

<210> SEQ ID NO 20
<211> LENGTH: 30
<212> TYPE: DNA
<213> ORGANISM: Artificial Sequence
<220> FEATURE:
<223> OTHER INFORMATION: probes and primers for amplification

<400> SEQUENCE: 20
attccgccaa tacacaacaa ccaataaacg                                      30

<210> SEQ ID NO 21
<211> LENGTH: 19
<212> TYPE: DNA
<213> ORGANISM: Artificial Sequence
<220> FEATURE:
<223> OTHER INFORMATION: probes and primers for amplification

<400> SEQUENCE: 21
ttcccgccgc tataaatcg                                                  19

<210> SEQ ID NO 22
<211> LENGTH: 23
<212> TYPE: DNA
<213> ORGANISM: Artificial Sequence
<220> FEATURE:
<223> OTHER INFORMATION: probes and primers for amplification

<400> SEQUENCE: 22
gttagttagc gttttagggt cga                                             23

<210> SEQ ID NO 23
<211> LENGTH: 24
<212> TYPE: DNA
<213> ORGANISM: Artificial Sequence
<220> FEATURE:
<223> OTHER INFORMATION: probes and primers for amplification

<400> SEQUENCE: 23
ccaactcgcg actcgaatcc ccga                                            24

<210> SEQ ID NO 24
<211> LENGTH: 19
<212> TYPE: DNA
<213> ORGANISM: Artificial Sequence
<220> FEATURE:
<223> OTHER INFORMATION: probes and primers for amplification
```

```
<400> SEQUENCE: 24
acgacgacga aacctctcg                                                19

<210> SEQ ID NO 25
<211> LENGTH: 31
<212> TYPE: DNA
<213> ORGANISM: Artificial Sequence
<220> FEATURE:
<223> OTHER INFORMATION: probes and primers for amplification

<400> SEQUENCE: 25
gggagttgta gtttagttag ttagggagta g                                  31

<210> SEQ ID NO 26
<211> LENGTH: 20
<212> TYPE: DNA
<213> ORGANISM: Artificial Sequence
<220> FEATURE:
<223> OTHER INFORMATION: probes and primers for amplification

<400> SEQUENCE: 26
tttttattcg tcgggaggag                                               20

<210> SEQ ID NO 27
<211> LENGTH: 20
<212> TYPE: DNA
<213> ORGANISM: Artificial Sequence
<220> FEATURE:
<223> OTHER INFORMATION: probes and primers for amplification

<400> SEQUENCE: 27
cccgcgatta aactcgaaaa                                               20
```

HYPERMETHYLATION BIOMARKERS FOR DETECTION OF HEAD AND NECK SQUAMOUS CELL CANCER

CROSS-REFERENCE TO RELATED APPLICATIONS

This application is a 35 U.S.C. 371 U.S. national entry of International Application PCT/US2011/028011, having an international filing date of Mar. 11, 2011, which claims the benefit of U.S. Provisional Application No. 61/313,383, filed Mar. 12, 2010, the content of each of the aforementioned applications is herein incorporated by reference in their entirety.

This invention was made using funds from the U.S. government. Under the terms of grant no. U01 CA84986 from the National Cancer Institute, the U.S. government retains certain rights in the invention.

TECHNICAL FIELD OF THE INVENTION

This invention is related to the area of head and neck cancer. In particular, it relates to detection and characterization of head and neck cancer.

BACKGROUND OF THE INVENTION

There are an estimated half a million cases of oral and oropharyngeal cancer worldwide. [1] Oral cavity mortality rates have remained unchanged or have decreased in some countries around the world from 1995 to 2005. [2] It is well established that oral cancer incidence and mortality are higher in regions where tobacco habits, in the form of chewing and/or smoking, with or without alcohol intake, are common. [3] It is also known that oral cancer cases distribution and occurrence varies by age, ethnic group, culture and life style, and level of country development. [4] For example, the Population Attributable Risk (PAR) due to the effects of tobacco and alcohol on oral cavity cancers is lower in the United States (US) than in Europe and Latin America. [5]

While incidence and mortality rates are relatively low compared to other cancers, oral cancer patients are usually diagnosed in an advanced stage, which is associated with worse prognosis and higher radio- and chemotherapy morbidity. Moreover, the oral cavity patient quality of life is disproportionately compromised, since surgical therapy can be mutilating and often has significant effects on swallowing, speech, and physical appearance. [6] Evidently, improved oral cancer prevention, early detection, diagnostic, and clinical management tools are needed to identify high risk patients, such as patients with smoking and alcohol exposures, patients without adequate access to health care, and patients with high risk lesions such as leukoplakia, which may progress to carcinoma lesions.[7]

Quantitative Methylation Specific PCR (qMSP) has been proposed as a platform to develop early detection, diagnostic, and clinical management biomarkers in Head and Neck Squamous Cell Carcinoma (HNSCC).[8-10] However, previous efforts at identifying epigenomic biomarkers in HNSCC have been limited by candidate gene or cell culture-based discovery approaches and validation technologies on well characterized pathology specimens from homogeneous cohorts, all of which has limited the clinical relevance of the results. [11-13] Numerous genes in OSCC tissues have been studied for promoter methylation status. It has also been shown that histologically normal tissue adjacent to tumors and premalignant lesions can also have high levels of methylation of some genes, suggesting that methylation is an early event in oral carcinogenesis [14]. Hypermethylated genes in OSCC have been associated with alterations in proliferation, DNA repair, apoptosis, cell-cell adhesion and angiogenesis, Clinically, they have been associated with tumor aggressiveness, invasiveness and with the malignant transformation of oral epithelial dysplasia [14]. Recently, our lab showed that promoter hypermethylation is present in OSCC premalignant lesions, is useful for HNSCC detection and plays a role in the development of resistance to cytotoxic chemotherapeutic agents [15-18]. Other laboratories have shown that promoter methylation of genes in saliva may serve as potential biomarkers for early detection of primary and relapsing OSCC/HNSCC [19, 20].

Pharmacologic unmasking in cell lines with subsequent validation in surgical specimens has been the canonical pseudo genome-wide discovery approach used to identify differentially genes in OSCC.[21] This approach has provided a description of hypermethylated and silenced tumor suppressor genes or hypomethylated candidate proto-oncogenes, in well characterized and carefully dissected samples from, in the large part, North American patients.[22, 23] The results obtained with the pharmacologic unmasking approach in cell lines however have shown poor clinical application, probably due to pharmacologic bias and methylation changes associated to cell lines passage, as well as the high degree of cellular heterogeneity in tumor tissue and saliva samples.

The advent of high throughput genomic platforms provides the opportunity to examine novel approaches. We set out to overcome the limitations of previous methods using a novel study design in clinically defined samples from populations with different risk profiles. [24-26] We used high-density promoter methylation platforms, publicly available expression arrays, and qMSP in a Phase I Biomarker Development Trial to identify differentially methylated genes that can distinguish between OSCC/HNSCC tumor and normal tissue in study populations with different risk factors. [8, 27, 28] A novel feature of this project, which facilitates the heterogeneous risk factor approach, is the two-stage design of the study. In the first stage, called the Discovery Screen, we used clinical samples obtained from Spain, a population with high OSCC risk associated to tobacco smoking and alcohol consumption. [29, 30] In the second stage, called the "Prevalence Screen," we analyzed the promoter methylation status of the best performing hypermethylated genes identified in the Discovery Screen on DNA isolated from a separate cohort of HNSCC tumor samples from North America with well characterized histopathology. Markers that perform well in a population with a heterogeneous risk profile in a clinical setting in the Discovery screen have a higher probability of performing well in a well-characterized set of confirmed cases and controls in the Prevalence screen. This novel study design maximizes resource investment in Phase I Biomarker Development Trials (BDT) and ensures that more robust biomarkers are tested in Phase II. Bioinformatics, biostatistical and pathway analyses were used to identify relevant genes and Quantitative Methylation Specific PCR (qMSP) was used to determine the differential methylation identified in particular genes or pathways. There is a continuing need in the art to develop sensitive and accurate detection of cancers at an early stage.

SUMMARY OF THE INVENTION

According to one aspect of the invention a method is provided for identifying head and neck squamous cell cancer. Epigenetic silencing of at least one gene selected from the group consisting of HOXA9, NID2, MCAM, EDNRB, CALCA, KIF1a, GATA4, and DCC is detected in a test sample containing head and neck squamous cells or nucleic acids from head and neck squamous cell cells. The test sample is identified as containing cells that are neoplastic or as containing nucleic acids from cells that are neoplastic.

According to another aspect of the invention a kit is provided for assessing head and neck squamous cell cancer in a test sample that contains head and neck squamous cells or nucleic acids from head and neck squamous cells. The kit comprises in a package a reagent that (a) modifies methylated cytosine residues but not non-methylated cytosine residues, or that (b) modifies non-methylated cytosine residues but not methylated cytosine residues; and at least one pair of oligonucleotide primers that specifically hybridizes under amplification conditions to a region of a gene selected from the group of genes consisting of HOXA9, NID2, MCAM, EDNRB, CALCA, KIF1a, GATA4, and DCC. The region to which the primers specifically hybridize is within about 1 kb of the gene's transcription start site. The kit also contains instructions for assessing head and neck squamous cell cancer using the reagents.

According to still another aspect of the invention a kit is provided for assessing head and neck squamous cell cancer in a test sample that contains head and neck squamous cells or nucleic acids from head and neck squamous cells. The kit comprises in a package at least two pairs of oligonucleotide primers that specifically hybridize under amplification conditions to a region of a gene selected from the group of genes consisting of HOXA9, NID2, MCAM, EDNRB, CALCA, KIF1a, GATA4, and DCC. The region to which the primers specifically hybridize is within about 1 kb of the selected gene's transcription start site. Instructions for assessing head and neck squamous cell cancer using the primers are also included with the kit.

According to another aspect head and neck squamous cell cancer is characterized. A test sample comprising head and neck squamous cells or nucleic acids from head and neck squamous cell cells, is tested for epigenetic silencing of at least one gene selected from the group consisting of HOXA9, NID2, MCAM, EDNRB, CALCA, KIF1a GATA4, and DCC. The presence or amount of epigenetic silencing characterizes the cancer.

These and other embodiments which will be apparent to those of skill in the art upon reading the specification provide the art with methods and tools for assessment of clinical samples for the presence or amounts or types of cancer cells or nucleic acids.

BRIEF DESCRIPTION OF THE DRAWINGS

FIG. 2A-2G. FIG. 2A shows unsupervised hierarchical clustering based on the unweighted average method using correlation as the similarity measure and ordering by average values. Different colors were selected to represent hypermethylated genes and hypomethylated genes. Normal mucosa, leukoplakia, and oral squamous cell carcinoma samples were examined using the HumanMethylation27 DNA Analysis BeadChip assay, which interrogates 27,578 CpG sites from 14,495 protein-coding gene promoters and 110 micro-RNA gene promoters. FIG. 2B shows a closer examination of differential methylation in a subset of genes show a progression to hypermethylation in OSCC samples when compared to normal and leukoplakia samples, FIG. 2C shows Venn diagrams indicating the overlap of significantly hypermethylated genes in cancer when compared to normal tissue, genes hypermethylated leukoplakia when compared to normal mucosa, and hypermethylated genes in tumor when compared to leukoplakia tissue. FIG. 2D shows Venn diagrams indicating the overlap of significantly hypomethylated genes in tumor when compared to normal samples, genes hypomethylated in leukoplakia when compared to normal tissue, and genes hypomethylated in leukoplakia when compared to normal tissue. FIG. 2E shows the progression of differential methylation events between the three groups of tissue examined with the Infinium methylation assay: normal oral mucosa, leukoplakia and OSCC tissues. The number of potential tumor suppressor genes and potential proto-oncogenes are shown for every two-way comparison between the three histology groups. FIG. 2F shows a bar graph showing the chromosomal frequency of hypermethylated genes in OSCC when compared to normal mucosa. The majority of the 301 hypermethylated genes are clustered from chromosome 1 to chromosome 11. FIG. 2G shows a bar graph indicating the chromosomal frequency of hypomethylated genes in OSCC when compared to normal mucosa. The majority of the 62 hypomethylated genes are clustered between chromosome 8 and chromosome 19.

FIG. 3A provides a volcano plot of p-values versus effect size in the expression arrays. The $\log_{10}$ of the Fold Change P value of tumor vs. control from the 9,441 upregulated genes are plotted to the right of the 0 effect size value in center and log 10 of the Fold Change P value of tumor vs. control from the 8,356 downregulated genes are plotted to the left. The 301 significantly hyper methylated genes in OSCC were depicted in a color: 140 genes are plotted to the left and 161 are plotted to the right of 0 effect size in the center. The Y axis represents the log of the Fold Change P value of tumor vs. control. The X axis represents the $\log_2$ fold change of tumor vs. control. FIG. 3B provides a Venn diagram shows the overlapping 140 genes, significantly hypermethylated in the methylation platforms and significantly downregulated in the expression arrays.

FIG. 5A provides scatterplots of quantitative MSP analysis of candidate genes promoters in the Prevalence screen cohort, which consisted of 55 HNSCC tumor tissue samples and 37 normal tissue samples obtained from uvulopharyngopalatoplasty (UPPP) procedures performed in non-cancer patients. The relative level of methylated DNA for each gene in each sample was determined as a ratio of MSP for the amplified gene to ACTB and then multiplied by 100 [(average value of duplicates of gene of interest/average value of duplicates of ACTB)×100] for HOXA9 and NID2. Horizontal line denotes cutoff value. FIG. 5B shows a Receiver Operator Characteristics (ROC) curve of HOXA9 line) and NID2 (dashed line) methylation in a HNSCC prevalence cohort (n=92).

FIG. 6. shows quantitative MSP primers and probes for ACTB (SEQ ID NO: 1-3), DCC (SEQ ID NO: 4-6), KIF1A (SEQ ID NO:7-9), NID2 (SEQ ID NO: 10-12), HOXA9

Figure 1:
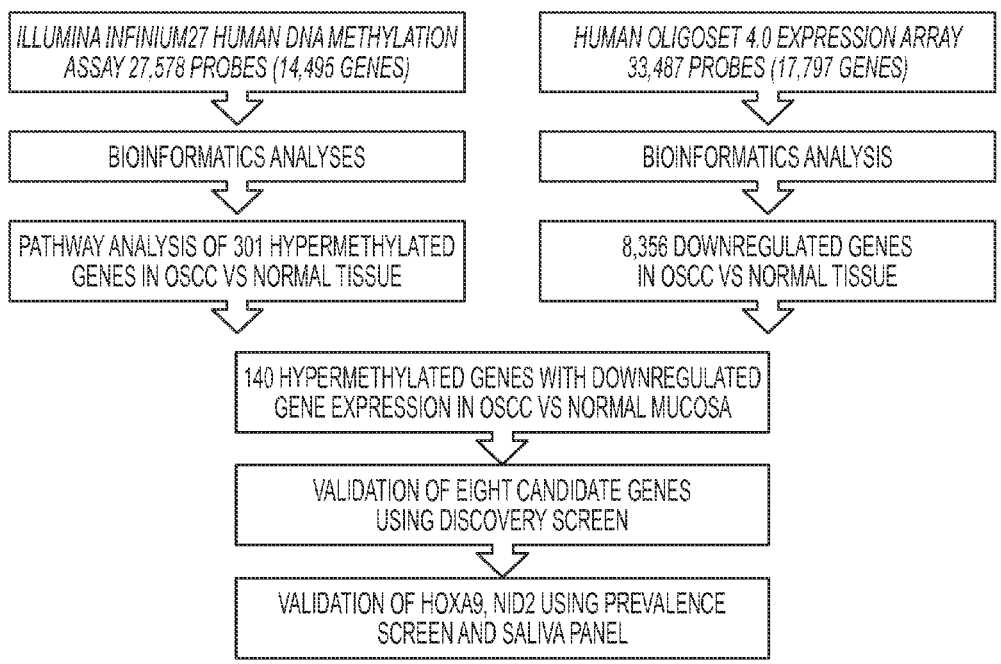
FIG. 1 shows a flowchart of the data analysis and integration tasks performed to identify HOXA9 and NID2 as two novel hypermethylated genes in OSCC and HNSCC.

(SEQ ID NO: 13-15), MCAM (SEQ ID NO: 16-18), CALCA (SEQ ID NO: 19-21), GATA4 (SEQ ID NO: 22-24), and EDNR (SEQ ID NO: 25-27).

DETAILED DESCRIPTION OF THE INVENTION

The inventors have developed a set of biomarkers that can be used alone or in combinations to assess the presence of and characterize head and neck squamous cell carcinoma, an in particular oral squamous cell carcinoma. While the inventors do not intend to be bound by any theories of mechanism of action, the biomarkers which are hypermethylated and hypoexpressed in cancer cells, may be tumor suppressors.

Because of the heterogeneity of tumors from individual to individual, even tumors of the same organ or type, any single marker may not yield sufficient sensitivity. Thus it may be beneficial to use panels of markers to increase the sensitivity of detection. One particular panel of markers that may be used for detection of head and neck squamous cell carcinoma and in particular oral squamous cell carcinoma comprises HOXA9 and NID2.

Tests can be carried out on any suitable sample that is likely to yield squamous cells or squamous cell nucleic acids. Particular samples which can be used include tissue specimens, biopsy specimens, surgical specimens, saliva, nasal mucosa, leukoplakia, erythroplakia, leukoerythroplakia and cytological specimens. It may be beneficial to extract nucleic acids from the cells prior to testing. Some techniques of testing may not require pre-extraction. Some testing may be done on proteins which may or may not be extracted from the cells prior to testing for particular detection techniques.

Any tests can be used to detect either hypermethylation, hypoexpression, or both. Suitable tests which can be used without limitation include lab-on-chip technology, microfluidic technologies, biomonitor technology, proton recognition technologies (e.g., Ion Torrent), and other highly parallel and/or deep sequencing methods. Once a biomarker is known as epigenetically silenced, either hypermethylation or hypoexpression may be used as in indicator of silencing.

Epigenetic modification of a gene can be determined by any method known in the art. One method is to determine that a gene which is expressed in normal cells or other control cells is less expressed or not expressed in tumor cells, hypoexpressed or silenced. This method does not, on its own, however, prove that the silencing or activation is epigenetic, as the mechanism of the silencing or inactivation could be genetic, for example, by somatic mutation. One method to determine that silencing is epigenetic is to treat with a reagent, such as DAC (5'-deazacytidine), or with a reagent which changes the histone acetylation status of cellular DNA or any other treatment affecting epigenetic mechanisms present in cells, and observe that the silencing is reversed, i.e., that the expression of the gene is reactivated or restored. Another means to determine epigenetic modification is to determine the presence of methylated CpG dinucleotide motifs in the silenced gene or the absence of methylation CpG dinucleotide motifs in the activated gene. Typically these methylated motifs reside near the transcription start site, for example, within about 3 kbp, within about 2.5 kbp, within about 2 kbp, within about 1.5 kbp, within about 1 kbp, within about 750 bp, or within about 500 bp. Once a gene has been identified as the target of epigenetic modification in tumor cells, determination of reduced or enhanced expression can be used as an indicator of epigenetic modification.

Expression of a gene can be assessed using any means known in the art. Typically expression is assessed and compared in test samples and control samples which may be normal, non-malignant cells. The test samples may contain cancer cells or pre-cancer cells or nucleic acids from them. Samples will desirably contain squamous Samples may contain mixtures of different types and stages of cancer cells. Either mRNA (or cDNA) or protein can be measured to detect expression which may be used as an indicator of epigenetic modification. Methods employing hybridization to nucleic acid probes can be employed for measuring specific mRNAs. Such methods include using nucleic acid probe arrays (microarray technology), in situ hybridization, and using Northern blots. Messenger RNA can also be assessed using amplification techniques, such as RT-PCR. Advances in genomic technologies now permit the simultaneous analysis of thousands of genes, although many are based on the same concept of specific probe-target hybridization. Sequencing-based methods are an alternative; these methods may be based on short tags, such as serial analysis of gene expression (SAGE) and massively parallel signature sequencing (MPSS). Differential display techniques provide yet another means of analyzing gene expression; this family of techniques is based on random amplification of cDNA fragments generated by restriction digestion, and bands that differ between two tissues identify cDNAs of interest.

Specific proteins can be assessed using any convenient method including immunoassays, immunohistochemistry, and immunocytochemistry but are not limited to that. Most such methods will employ antibodies which are specific for the particular protein or protein fragments. The sequences of the mRNA (cDNA) and proteins of the markers of the present invention are known in the art and publicly available.

Methylation-sensitive restriction endonucleases can be used to detect methylated CpG dinucleotide motifs. Such endonucleases may either preferentially cleave methylated recognition sites relative to non-methylated recognition sites or preferentially cleave non-methylated relative to methylated recognition sites. Examples of the former are Acc Ban I, BstN I, Msp I, and Xma I. Examples of the latter are Acc II, Ava I, BssH II, BstU I, Hpa II, and Not I. Alternatively, chemical reagents can be used which selectively modify either the methylated or non-methylated form of CpG dinucleotide motifs.

Modified products can be detected directly, or after a further reaction which creates products which are easily distinguishable. Means which detect altered size and/or charge can be used to detect modified products, including but not limited to electrophoresis, chromatography, and mass spectrometry. Examples of such chemical reagents for selective modification include hydrazine and bisulfite ions. Hydrazine-modified DNA can be treated with piperidine to cleave it. Bisulfite ion-treated DNA can be treated with alkali. Other means which rely on specific sequences can be used, including but not limited to hybridization, amplification, sequencing, and ligase chain reaction, Combinations of such techniques can be uses as is desired.

The principle behind electrophoresis is the separation of nucleic acids via their size and charge. Many assays exist for detecting methylation and most rely on determining the presence or absence of a specific nucleic acid product. Gel electrophoresis is commonly used in a laboratory for this purpose.

One may use MALDI mass spectrometry in combination with a methylation detection assay to observe the size of a nucleic acid product. The principle behind mass spectrometry is the ionizing of nucleic acids and separating them according to their mass to charge ratio. Similar to electrophoresis, one can use mass spectrometry to detect a specific nucleic acid that was created in an experiment to determine methylation.

One form of chromatography, high performance liquid chromatography, is used to separate components of a mixture based on a variety of chemical interactions between a substance being analyzed and a chromatography column. DNA is first treated with sodium bisulfite, which converts an unmethylated cytosine to uracil, while methylated cytosine residues remain unaffected. One may amplify the region containing potential methylation sites via PCR and separate the products via denaturing high performance liquid chromatography (DHPLC). DHPLC has the resolution capabilities to distinguish between methylated (containing cytosine) and unmethylated (containing uracil) DNA sequences.

Hybridization is a technique for detecting specific nucleic acid sequences that is based on the annealing of two complementary nucleic acid strands to form a double-stranded molecule. One example of the use of hybridization is a microarray assay to determine the methylation status of DNA. After sodium bisulfite treatment of DNA, which converts an unmethylated cytosine to uracil while methylated cytosine residues remain unaffected, oligonucleotides complementary to potential methylation sites can hybridize to the bisulfite-treated DNA. The oligonucleotides are designed to be complimentary to either sequence containing uracil (thymine) or sequence containing cytosine, representing unmethylated and methylated DNA, respectively. Computer-based microarray technology can determine which oligonucleotides hybridize with the DNA sequence and one can deduce the methylation status of the DNA. Similarly primers can be designed to be complimentary to either sequence containing uracil (thymine) or sequence containing cytosine. Primers and probes that recognize the converted methylated form of DNA are dubbed methylation-specific primers or probes (MSP).

An additional method of determining the results after sodium bisulfite treatment involves sequencing the DNA to directly observe any bisulfite-modifications. Pyrosequencing technology is a method of sequencing-by-synthesis in real time. It is based on an indirect bioluminometric assay of the pyrophosphate (PPi) that is released from each deoxynucleotide (dNTP) upon DNA-chain elongation. This method presents a DNA template-primer complex with a dNTP in the presence of an exonuclease-deficient Klenow DNA polymerase. The four nucleotides are sequentially added to the reaction mix in a predetermined order. If the nucleotide is complementary to the template base and thus incorporated, PPi is released. The PPi and other reagents are used as a substrate in a luciferase reaction producing visible light that is detected by either a luminometer or a charge-coupled device. The tight produced is proportional to the number of nucleotides added to the DNA primer and results in a peak indicating the number and type of nucleotide present in the form of a pyrogram. Pyrosequencing can exploit the sequence differences that arise following sodium bisulfite-conversion of DNA.

A variety of amplification techniques may be used in a reaction for creating distinguishable products. Some of these techniques employ PCR. Other suitable amplification methods include the ligase chain reaction (LCR) (Barringer et al, 1990), transcription amplification (Kwoh et al. 1989; WO88/10315), selective amplification of target polynucleotide sequences (U.S. Pat. No. 6,410,276), consensus sequence primed polymerase chain reaction (U.S. Pat. No. 4,437,975), arbitrarily primed polymerase chain reaction (WO90/06995), nucleic acid based sequence amplification (NASBA) (U.S. Pat. Nos. 5,409,818; 5,554,517; 6,063,603), microsatellite length polymorphism (MLP), and nick displacement amplification (WO2004/067726).

Sequence variation that reflects the methylation status at CpG dinucleotides in the original genomic DNA offers two approaches to PCR primer design. In the first approach, the primers do not themselves "cover" or hybridize to any potential sites of DNA methylation; sequence variation at sites of differential methylation are located between the two primers. Such primers are used in bisulfite genomic sequencing, COBRA, Ms-SNuPE. In the second approach, the primers are designed to anneal specifically with either the methylated or unmethylated version of the converted sequence. If there is a sufficient region of complementarity, e.g., 12, 15, 18, or 20 nucleotides, to the target, then the primer may also contain additional nucleotide residues that do not interfere with hybridization but may be useful for other manipulations. Exemplary of such other residues may be sites for restriction endonuclease cleavage, for ligand binding or for factor binding or linkers or repeats. The oligonucleotide primers may or may not be such that they are specific for modified methylated residues One way to distinguish between modified and unmodified DNA is to hybridize oligonucleotide primers which specifically bind to one form or the other of the DNA. After hybridization, an amplification reaction can be performed and amplification products assayed. The presence of an amplification product indicates that a sample hybridized to the primer. The specificity of the primer indicates whether the DNA had been modified or not, which in turn indicates whether the DNA had been methylated or not. For example, bisulfite ions modify non-methylated cytosine bases, changing them to uracil bases. Uracil bases hybridize to adenine bases under hybridization conditions. Thus an oligonucleotide primer which comprises adenine bases in place of guanine bases would hybridize to the bisulfite-modified DNA, whereas an oligonucleotide primer containing the guanine bases would hybridize to the non-modified (methylated) cytosine residues in the DNA. Amplification using a DNA polymerase and a second primer yield amplification products which can be readily observed. Such a method is termed MSP (Methylation Specific PCR; U.S. Pat. Nos. 5,786,146; 6,017,704; 6,200,756). The amplification products can be optionally hybridized to specific oligonucleotide probes which may also be specific for certain products. Alternatively, oligonucleotide probes can be used which will hybridize to amplification products from both modified and nonmodified DNA.

Another way to distinguish between modified and non-modified DNA is to use oligonucleotide probes which may also be specific for certain products. Such probes can be hybridized directly to modified DNA or to amplification products of modified DNA. Oligonucleotide probes can be labeled using any detection system known in the art. These include but are not limited to fluorescent moieties, radioisotope labeled moieties, bioluminescent moieties, luminescent moieties, chemiluminescent moieties, enzymes, substrates, receptors, or ligands.

Still another way for the identification of methylated CpG dinucleotides utilizes the ability of the MBD domain of the McCP2 protein to selectively bind to methylated DNA sequences (Cross et al, 1994; Shiraishi et al, 1999). Restriction endonuclease digested genomic DNA is loaded onto expressed His-tagged methyl-CpG binding domain that is immobilized to a solid matrix and used for preparative column chromatography to isolate highly methylated DNA sequences.

Real time chemistry allows for the detection of PCR amplification during the early phases of the reactions, and makes quantitation of DNA and RNA easier and more precise. A few variations of the real-time PCR are known. They include the TaqMan™ (Roche Molecular Systems) system and Molecular Beacon™ system which have separate probes labeled with a fluorophore and a fluorescence quencher. In the Scorpion™ system the labeled probe in the form of a hairpin structure is linked to the primer. In addition, the Amplifluor™ (Chemicon International) system and the Plexor™ (Promega) system can be used.

DNA methylation analysis has been performed successfully with a number of techniques which include the MALDI-TOFF, MassARRAY, MethyLight, Quantitative analysis of ethylated alleles (QAMA), enzymatic regional methylation assay (ERMA), HeavyMethyl, QBSUPT, MS-SNuPE, MethylQuant, Quantitative PCR sequencing, and Oligonucleotide-based microarray systems.

The number of genes whose modification is tested and/or detected can vary: one, two, three, four, five, or more genes can be tested and/or detected. In some cases at least two genes are selected. In other embodiments at least three genes are selected.

Testing can be performed diagnostically or in conjunction with a therapeutic regimen. Testing can be used to monitor efficacy of a therapeutic regimen, for example, whether a chemotherapeutic agent or a biological agent, such as a polynucleotide. Testing can also be used to determine what therapeutic or preventive regimen to employ on a patient. Moreover, testing can be used to stratify patients into groups for testing agents and determining their efficacy on various groups of patients. Such uses characterize the cancer into categories based on the genes which are epigenetically silenced and/or the amount of silencing of the genes. In the case of a diagnosis or characterization, information comprising data or conclusions can be written or communicated electronically or orally. The identification may be assisted by a machine. Communication of the data or conclusions may be from a clinical laboratory to a clinical office, from a clinician to a patient, or from a specialist to a generalist, as examples. The form of communication of data or conclusions typically may involve a tangible medium or physical human acts.

A test sample obtainable from tissue or cell specimens or fluids includes detached tumor cells and/or free nucleic acids that are released from dead or damaged tumor cells. Nucleic acids include RNA, genomic DNA, mitochondrial DNA, single or double stranded, and protein-associated nucleic acids. Any nucleic acid specimen in purified or non-purified form obtained from such specimen cell can be utilized as the starting nucleic acid or acids. The test samples may contain cancer cells or pre-cancer cells or nucleic acids from them.

Demethylating agents can be contacted with cells in vitro or in vivo for the purpose of restoring normal gene expression to the cell or for validation of methylation. Suitable demethylating agents include, but are not limited to 5-aza-2'-deoxycytidine, 5-aza-cytidine, Zebularine, procaine, and L-ethionine. This reaction may be used for diagnosis, for determining predisposition, and for determining suitable therapeutic regimes.

Although diagnostic and prognostic accuracy and sensitivity may be achieved by using a combination of markers, such as 5 or 6 markers, or 9 or 10 markers, practical considerations may dictate use of smaller combinations. Any combination of markers for a specific cancer may be used which comprises 2, 3, 4, or 5 markers. Combinations of 2, 3, 4, or 5 markers can be readily envisioned given the specific disclosures of individual markers provided herein.

Kits according to the present invention are assemblies of reagents for testing methylation and/or silencing. They are typically in a package which contains all elements, optionally including instructions. Instructions may be in any form, including paper or digital. The instructions may be on the inside or the outside of the package. The instructions may be in the form of an interact address which provides the detailed manipulative or analystic techniques. The package may be divided so that components are not mixed until desired. Components may be in different physical states. For example, some components may be lyophilized and some in aqueous solution. Some may be frozen. Individual components may be separately packaged within the kit. The kit may contain reagents, as described above for differentially modifying methylated and non-methylated cytosine residues. Desirably the kit will contain oligonucleotide primers which specifically hybridize to regions within 1 kb of the transcription start sites of the selected genes/biomarkers. Additional markers may be used. Typically the kit will contain both a forward and a reverse primer for a single gene or marker. If there is a sufficient region of complementarity, e.g., 12, 15, 18, or 20 nucleotides, then the primer may also contain additional nucleotide residues that do not interfere with hybridization but may be useful for other manipulations. Exemplary of such other residues may be sites for restriction endonuclease cleavage, for ligand binding or for factor binding or linkers or repeats. The oligonucleotide primers may or may not be such that they are specific for modified methylated residues. The kit may optionally contain oligonucleotide probes. The probes may be specific for sequences containing modified methylated residues or for sequences containing non-methylated residues. The kit may optionally contain reagents for modifying methylated cytosine residues. The kit may also contain components for performing amplification, such as a DNA polymerase (particularly a thermostable DNA polymerase) and deoxyribonucleotides, labeled or not. Means of detection may also be provided in the kit, including detectable labels on primers or probes. Kits may also contain reagents for detecting gene expression. Such reagents may include probes, primers, or antibodies, for example. In the case of enzymes or ligands, substrates or binding partners may be used to assess the presence of the marker. Kits may contain 1, 2, 3, 4, or more of the primers or primer pairs of the invention. Kits that contain probes may have them as separate molecules or covalently linked to a primer for amplifying the region to which the probes hybridize. Other useful tools for performing the methods of the invention or associated testing, therapy, or calibration may also be included in the kits, including buffers, enzymes, gels, plates, detectable labels, vessels, etc. Kits may include tools for collecting suitable samples, such as tools for collecting oral swabs, oral biopsies, and endoscopes.

As an example, a gene may be contacted with hydrazine, which modifies cytosine residues, but not methylated cytosine residues. Then the hydrazine-treated gene sequence may be contacted with a reagent such as piperidine, which cleaves the nucleic acid molecule at hydrazine modified cytosine residues, thereby generating a product comprising fragments. By separating the fragments according to molecular weight, using, for example, an electrophoretic, chromatographic, or mass spectrographic method, and comparing the separation pattern with that of a similarly treated corresponding non-methylated gene sequence, gaps are apparent at positions in the test gene contained methylated cytosine residues. The presence of gaps is indicative of methylation of a cytosine residue in the CpG dinucleotide in the target gene of the test cell.

Bisulfite ions, for example, sodium bisulfite, convert non-methylated cytosine residues to bisulfite modified cytosine residues. The bisulfite ion treated gene sequence can be exposed to alkaline conditions, which convert bisulfite modified cytosine residues to uracil residues. Sodium bisulfite reacts readily with the 5,6-double bond of cytosine (but poorly with methylated cytosine) to form a sulfonated cytosine reaction intermediate that is susceptible to deamination, giving rise to a sulfonated uracil. The sulfonate group can be removed by exposure to alkaline conditions, resulting in the formation of uracil. The DNA can be amplified, for example, by PCR, and sequenced to determine whether CpG sites are methylated in the DNA of the sample. Uracil is recognized as a thymine by Taq polymerase and, upon PCR, the resultant product contains cytosine only at the position where 5-methylcytosine was present in the starting template DNA. One can compare the amount or distribution of uracil residues in the bisulfite ion treated gene sequence of the test cell with a similarly treated corresponding non-methylated gene sequence. A decrease in the amount or distribution of uracil residues in the gene from the test cell indicates methylation of cytosine residues in CpG dinucleotides in the gene of the test cell. The amount or distribution of uracil residues also can be detected by contacting the bisulfite ion treated target gene sequence, following exposure to alkaline conditions, with an oligonucleotide that selectively hybridizes to a nucleotide sequence of the target gene that either contains uracil residues or that lacks uracil residues, but not both, and detecting selective hybridization (or the absence thereof) of the oligonucleotide.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

To our knowledge this is the first study that utilizes an unbiased genome-wide DNA methylation platform to uncover differentially methylated genes in OSCC. We successfully implemented a novel approach that combines high-density promoter methylation platforms, together with publicly available methylation and gene expression array data, to identify novel hypermethylated genes in OSCC and HNSCC. These candidate genes can be used in diagnostic panels for early detection of OSCC and HNSCC in tissue and saliva from patients from countries with different PAR due to tobacco and alcohol use.

We used clinical rather than pathological characterization of our samples in the Discovery Screen and well characterized surgical samples in the Prevalence screen. By testing our candidate genes in samples from populations with different risk profiles we aimed to increase their clinical usefulness to both surgical and dental practitioners.

Our results suggest that patient heterogeneity in PAR to the two main risk factors for OSCC strengthens this molecular study, and may lead to a better reproducibility of the results in other populations. The focus of this study was not, however, to explore the potential associations of the novel hypermethylated genes we identified in this study with tobacco and alcohol consumption. We first wanted to establish the usefulness of using clinical samples from OSCC patients with heterogeneous risk profiles to identify hypermethylated genes that could distinguish between normal and tumor samples in Phase I Biomarker Development studies, utilizing unbiased genome-wide arrays.

Precancerous lesions of the upper aerodigestive tract include leukoplakia, erythroplakia and leukoerythroplakia. These are clinically defined lesions that have a higher degree of oncogenic risk when compared with normal oral mucosa. When these lesions show evidence of cellular atypia without evidence of invasion, they are defined as dysplastic. The presence of dysplasia increases the oncogenic risk of these lesions. Our focus in this project was to identify markers that may be useful for early diagnosis in populations with different risk profiles, and thus our interest in using samples from Europe in the Discovery screen and from North America in the Prevalence screen.

The significant differentially hypermethylated genes identified by our approach were found to be associated with oncogenic transformation pathways and cellular functions that are de-regulated in cancer: The changes identified by pathway and gene ontology analysis underlie the progressive acquisition of a malignant phenotype in OSCC progression, which should be looked into utilizing a pathway driven approach that is beyond the scope of this manuscript.

The heatmap revealed differential DNA methylation progression, distinguishing methylation or de-methylation events unique to each tissue type: normal, leukoplakia and tumor. Our integrative approach identified HOXA9 and NID2 as novel differentially methylated genes in OSCC in the Discovery Screen. These genes then proved to have significantly higher methylation levels in tumor than normal mucosa in the Prevalence screen, as evidenced by ROC analysis of HNSCC samples. This finding may find clinical applicability in OSCC/HNSCC resection margin assessment and in situations when an OSCC/HNSCC biopsy is non-conclusive such as in post chemo-radiation scenarios.

The evaluation of methylation of HOXA9 and NID2 in separate cohorts of salivary rinses from non-cancer individuals and patients with OSCC revealed high specificity values limited sensitivity, and an AUC of 0.77 for a panel of both genes. These results favorably compare to previous hypermethylated markers evaluated in saliva. [17] The fact that we observed much better sensitivity and AUC results in saliva from OSCC patients compared with saliva from OPSCC patients might result from two possible causes: the first may be due to the different risk factors associated with OSCC and OPSCC. A large proportion of OPSCC are HPV related as opposed to OSCC, which are smoking and alcohol related. It might very well be that viral related tumors have different patterns of methylation motifs than chemical related tumors. Another plausible cause is that saliva does not bathe the oropharynx in the same extent as it does the oral cavity and thus there is less representation of tumor tissue cells in the saliva compartment.

The functional role of NID2 and HOXA9 has not been investigated in OSCC/HNSCC. Nidogens are believed to connect laminin and collagen IV networks, hence stabilizing the basement membrane structure. Nidogens are also important for cell adhesion, as they establish contacts with various cellular integrins [36]. Loss of nidogen expression in OSCC may thus favor invasion and metastasis of tumor cells by loosening cell interaction with basal membrane and by weakening the strength of the basement membrane itself.

Functional studies have revealed that loss of HOXA9 promotes mammary epithelial cell growth and survival, as well as altered tissue morphogenesis. Restoring HOXA9 expression represses growth and survival and inhibits the malignant phenotype of breast cancer cells in culture and in xenograft mouse models. HOXA9 has been shown to restrict breast tumor behavior by directly modulating the expression of BRCA1, a DNA repair gene [38]. Therefore HOXA9 hypermethylation may lead to diminished DNA repair capacity in OSCC/HNSCC, thus increasing cancer risk particularly in those patients that smoke tobacco, which has been shown to lead to the formation of oncogenic DNA-PAH adducts [45].

We used the two most common statistical approaches utilized in biomarker studies: modeling disease risk with logistic regression models and evaluated biomarker performance by measuring sensitivity, specificity, ROC and the AUC. [46] We performed logistic regression modeling with one predictor to draw the predictive probability plots for each gene in the Discovery screen, the Prevalence screen, and the saliva screens. The predictor methylation is the QMSP value for each case (1) and each control (0). Cutoff methylation values for each gene are shown by vertical dotted line. The classification performance for HOXA9 and NID2 in both, HNSCC tissue and OSCC saliva were highly satisfactory and the best published so far for hypermethylated biomarkers HNSCC tissue and OSCC saliva, respectively.

The non-stochastic chromosomal location of hypermethylated and hypomethylated genes in the comparison between normal and OSCC tissue, as well as the similar comparisons with leukoplakia tissue, also deserves further research, which is beyond the context of this manuscript. The chromosomal location of the significant differential methylation events can be utilized to unravel the interplay between genetic and differential methylation in the progression from normal to OSCC tissue, contribute to the identification of novel therapeutic strategies for this malignancy, and help us understand whether OSCC exhibits oncogene addiction, [42, 43] and/or network/pathway addiction. This multi-dimensional knowledge may provide opportunities for the diagnosis of premalignant squamous lesions, and for the development of novel molecular-targeted strategies for the prevention and treatment of OSCC. [44]

In sum, the preliminary results suggest HOXA9 and NID2 are promising OSCC biomarkers that should be studied on tissue, saliva and serum from larger cohorts, as we move forward. These OSCC biomarkers may be useful in oral cancer prevention, early detection, diagnostic, and clinical management studies that target high risk patients, patients without adequate access to health care, and patients with high risk lesions such as leukoplakia, which may progress to carcinoma lesions. Our results in also suggest that a Phase I Biomarker development trial can be performed with a small number of genome-wide methylation arrays and subsequent validation in larger independent sample sets. A major feature facilitating our approach is the two-stage design of the study, which buffers the impact of sample-to-sample variance by using experimental and publicly available data sets. The two-stage design provides a sensitive approach for differential methylation and deregulated pathway detection in OSCC, while dramatically lowering the overall cost of a Phase I Biomarker development project. Resources can then be utilized on the validation of the initial findings in larger number of samples from independent cohorts.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLE 1

Methods
Patient Selection

Patients for this study were consented at hospitals in Baltimore, USA (n=143) and Madrid, Spain (n=36). Normal, premalignant and OSCC tumor tissue was collected from patients who visited the outpatient clinics of Hospital Gregorio Marañón in Madrid. OSCC tumor and adjacent tissue samples were collected at Hospital Ramon y Cajals in Madrid. Tumor and normal tissue and saliva rinses from HNSCC and healthy patients were collected at Johns Hopkins Hospital in Baltimore. Salivary rinses were obtained by rinse and gargle of 20 ml saline solution. All participants signed a consent form that clearly explained the risks and benefits of the study. The study was approved by the Ethics Committee of each participating hospital, as well as by the Johns Hopkins Institutional Review Board.

Samples

Tissue samples were frozen in liquid nitrogen and stored in −800 C. The salivary rinses were centrifuged, the supernatant was discarded and DNA was isolated from the pellet. Tissue samples were shipped to our laboratory at the Head and Neck Cancer Research Division of the Department of Otolaryngology at Johns Hopkins School of Medicine. Tissue (5 mg) and saliva pellets were digested with 1% SDS and 50 µg/mL proteinase K (Boehringer Mannheim) at 48° C. overnight, followed by phenol/chloroform extraction and ethanol precipitation of DNA as previously described.

Discovery Screen

Bisulfite modification of genomic DNA (2 ug) was performed with EpiTect Bisulfite Kit (QIAGEN) according to the manufacturer's protocol. We hybridized bisulfite converted DNA from normal (n=4), leukoplakia (n=4) and Oral Squamous Cell Carcinoma (OSCC) tissue (n=4) samples to the HumanMethylation27 DNA Analysis BeadChip assay, which quantitatively interrogates 27,578 CpG sites from 14,495 protein-coding gene promoters and 110 microRNA gene promoters at single-nucleotide resolution. The Infinium Methylation assay detects cytosine methylation at CpG islands based on highly multiplexed genotyping. The assay interrogates these chemically differentiated loci using two site-specific probes, one designed for the methylated locus (M bead type) and another for the unmethylated locus (U bead type). Single-base extension of the probes incorporates a labeled ddNTP, which is subsequently stained with a fluorescence reagent. A beta ($\beta$) value was used to denote the methylation level of the CpG loci using the ratio of intensities between methylated and unmethylated alleles ($\beta$ value=Methylation intensity/Methylation+unmethylated intensity of the given CpG locus).

Hierarchical Clustering Analysis and Heatmap Creation

The average beta values of all probes on the Illumina Infinium arrays were subjected to log 10 transformation and used to generate a heatmap based on unsupervised hierarchical clustering with Spotfire DecisionSite (Somerville, Mass.). This clustering was based on the unweighted average method using correlation as the similarity measure and ordering by average values. The color red was selected to represent hypermethylated genes and the color blue to represent hypomethylated genes.

Differential Methylation Bioinformatics

Bioinformatics strategies were used for background correction, normalization and data analysis of differentially methylated genomic regions between tumor, leukoplakia and normal tissue. The gene selection from the Illumina Infinium assay data was performed in a stepwise manner. An F-test was performed across all twelve samples to identify genes with a significant difference in $\beta$ values between normal, leukoplakia, and malignant tissue. Since the empirical p-values were calculated genome-wide, adjustment for multiple testing was performed. Rather than using a Bonferroni correction, which is very stringent, the p-values were transformed into q-values, which are measures of significance in terms of the false discovery rate (FDR) instead of the false positive rate normally associated with p-values. [31] Q-values were computed from the empirical p-values using the Benjamin and Hochberg correction. Probes with q-values less than 0.05 were deemed statistically significant and were included in the final gene list. We then selected only those genes that showed a methylation difference of at least 0.2 between cancer and normal tissues and a beta value of at least 0.3 in cancer. All bioinformatics analyses were performed using R version 2.11.1.

Comparison to Existing Databases of Known Methylation Events in Cancer

The list of differentially hypermethylated genes in tumor tissue identified in the Discovery Screen was first compared against existing databases of known methylation events in cancer. [32, 33] We generated a list of genes that have been previously shown to be hypermethylated in OSCC/HNSCC and in other tumor tissues.

Cross Reference of Hypermethylated Genes with Publicly Available OSCC Gene Expression Arrays We then searched the GEO database (NCBI) for published expression analyses, which compared favorably with our Infinium methylation assay in terms of analyzing OSCC tissues against normal oral tissues from healthy patients and not to adjacent normal oral tissues. GSE10121 hybridized 35 oral squamous cell carcinoma samples and 6 oral mucosa tissues from healthy participants to a whole-transcriptome spotted array that contains 35,035 gene-specific oligos (Human OligoSet 4.0). [34] The expression of genes identified to be hypermethylated in tumor tissue was examined for evidence of tumor down-regulation in the expression arrays and a list of genes showing both hypermethylation and down regulation was generated. (FIG. 1)

Ingenuity Pathway Analysis

Pathway and ontology analysis were performed to identify how differential methylation alters cellular networks and signaling pathways in OSCC. A list of RefSeq identifiers for hypermethylated/down-regulated genes was uploaded to the Ingenuity Pathway Analysis program (Redwood City, Calif.), enabling exploration of gene ontology and molecular interaction. Each uploaded gene identifier was mapped to its corresponding gene object (focus genes) in the Ingenuity Pathways Knowledge Base. Core networks were constructed for both direct and indirect interactions using default parameters, and the focus genes with the highest connectivity to other focus genes were selected as seed elements for network generation. New focus genes with high specific connectivity (overlap between the initialized network and gene's immediate connections) were added to the growing network until the network reached a default size of 35 nodes. Non-focus genes (those that were not among our differentially methylated input list) that contained a maximum number of links to the growing network were also incorporated. The ranking score for each network was then computed by a right-tailed Fisher's exact test as the negative log of the probability that the number of focus genes in the network is not due to random chance. Similarly, significances for functional enrichment of specific genes were also determined by the right-tailed Fisher's exact test, using all input genes as a reference set.

Validation of In-Silica Findings with Quantitative Methylation Specific PCR (qMSP)

qMSP was used to validate the candidate genes identified in the Discovery Screen on a cohort of oral cavity tissue samples from non-cancer and OSCC patients from Spain and the US. Briefly, bisulfite-modified DNA was used as template for fluorescence-based real-time PCR, as previously described. [35] Fluorogenic PCR reactions were carried out in a reaction volume of 20 μL consisting of 600 nmol/L of each primer; 200 μmol/L probe; 0.75 units platinum Taq polymerase (Invitrogen); 200 μmol/L of each dATP, dCTP, dGTP, and dTTP; 200 nmol/L ROX dye reference (Invitrogen); 16.6 mmol/L ammonium sulfate; 67 mmol/L Trizma (Sigma, St. Louis, Mo.); 6.7 mmol/L magnesium chloride; 10 mmol/L mercaptoethanol; and 0.1% DMSO. Duplicates of three microliters (3 μL) of bisulfite-modified DNA solution were used in each real-time methylation-specific PCR (MSP) amplification reaction. Primers and probes were designed to amplify a segment of a CpG island in the promoter of genes of interest and of a reference gene, actin-B (ACTB) as previously described. Primers and probes were tested on positive (genomic methylated bisulfite converted DNA) and negative controls (genomic unmethylated bisulfite converted DNA) to ensure amplification of the desired product and non-amplification of unmethylated DNA, respectively. Primer and probe sequences and annealing temperatures are provided in FIG. 6 (Supplementary Table 1).

Amplification reactions were carried out in 384-well plates in a 7900 Sequence Detector (Perkin-Elmer Applied Biosystems, Norwalk, Conn.) and were analyzed by SDS 2.2.1 (Sequence Detector System; Applied Biosystems, Norwalk, Conn.). Thermal cycling was initiated with a first denaturation step at 95° C. for 3 minutes, followed by 50 cycles of 95° C. for 15 seconds and annealing temperature for 1 minute. Each plate included patient DNA samples, positive (bisulfite converted hypermethylated universal DNA standard, Zymo Research) and multiple water blanks as non-template controls. Serial dilutions (60-0.006 ng) of this DNA were used to construct a calibration curve for each plate. The relative level of methylated DNA for each gene in each sample was determined as a ratio of qMSP for the amplified gene to ACTB and then multiplied by 100 for easier tabulation. The samples were categorized as unmethylated or methylated based on detection of methylation above a threshold set for each gene. This threshold was determined using ROC curves analyzing the levels and distribution of methylation, if any, in normal tissues.

Prevalence Screen

We then analyzed the promoter methylation status of the best performing hypermethylated genes found in the Discovery Screen on DNA from a set of well-characterized HNSCC tumor samples and healthy patients. This allowed the validation of the hypermethylated genes in an independent set of tumors, as well as provided an estimation of the hypermethylation prevalence among a larger number of tumors with well-characterized pathology. Furthermore, to examine the feasibility of creating a diagnostic panel we examined the promoter methylation status of the best performing candidate tumor suppressor genes in saliva samples from HNSCC and healthy patients.

Biostatistics

To test the reliability of using QMSP results to identify tumor tissue Cohen's kappa ($\kappa$) was used. Because there is no clear-cut "gold standard" for the QMSP results, equal weight was applied to promoter methylation for all genes. A $\kappa$ statistic <0 would suggest poor agreement, 0 to 0.20 slight, 0.21 to 0.40 fair, 0.41 to 0.60 moderate, 0.61 to 0.80 substantial, and 0.81 to 1.00 almost perfect. Confidence intervals (CI) were calculated for the kappa statistic using the STATA command "kapci." STATA uses an analytic method for simple two-by-two comparisons and a bootstrap method in the case of dichotomous variables. ROC curves were drawn to obtain sensitivity and specificity in the discovery screen and most suitable cut-off values were chosen. To measure the association between two QMSP results and tumor status the Chi-square statistic ($x2$) and Odds Ratios were calculated. The inverse-logit function logit-1 (x) was used to transform the QMSP results from continuous methylation values to probabilities in single predictor logistic regression models. Scatterplots, volcano plots and ROC, curves were drawn to describe the results. All Biostatistics analyses were performed using Stata 11 (Texas, USA) and R 2.11.1 (www.r-project.org).

EXAMPLE 2

Discovery Screen: Methylation Progression in OSCC

Figure 2C:
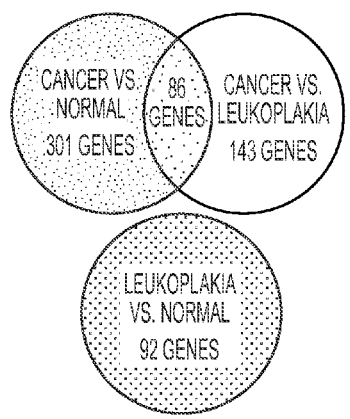

The bisulfite converted DNA from normal (n=4), leukoplakia (n=4) and Oral Squamous Cell Carcinoma (OSCC) tissue (n=4) samples was hybridized to the HumanMethylation27 DNA Analysis BeadChip assay, which quantitatively interrogates 27,578 CpG sites from 14,495 protein-coding gene promoters and 110 microRNA gene promoters at single-nucleotide resolution. The average beta values of all probes were log-transformed and used to generate a heatmap based on unsupervised hierarchical clustering. The clustering of all CpG loci (p<0.05) clearly distinguishes between methylation events in normal, leukoplakia, and oral cancer tissue. (FIG. 2a). Hypomethylated genes can be seen in blue and hypermethylated genes in red. A closer examination of differential methylation in a subset of genes shows a progression to hypermethylation in OSCC samples when compared to normal and leukoplakia samples. (FIG. 2b).

Figure 2D:
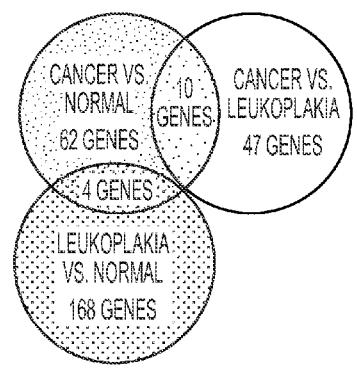
Figure 2E:
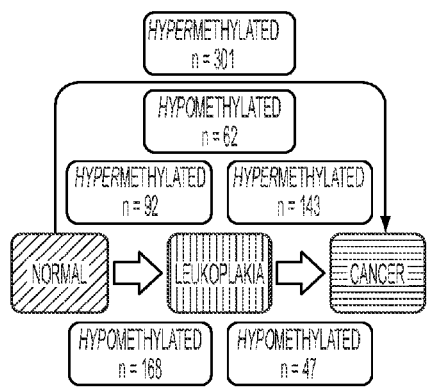

The bioinformatics strategy used to analyze the lumina data identified a progression of differential methylation events between the three tissue samples groups examined with the Infinium methylation assay. We observed 301 potential tumor suppressor genes that were significantly hypermethylated in cancer when compared to normal tissue, 92 genes hypermethylated in leukoplakia when compared to normal mucosa, and 143 hypermethylated genes in tumor when compared to leukoplakia tissue. There were 86 hypermethylated genes overlapping the 143 tumor/leukoplakia and 301 tumor/normal differentially methylated genes. (FIG. 2c) We also observed 62 potential (proto-oncogenes hypomethylated in tumor when compared to normal samples, 168 genes hypomethylated in leukoplakia when compared to normal tissue and 47 genes hypomethylated in leukoplakia when compared to tumor tissue. Ten genes overlapped the 62 cancer/normal and the 47 cancer/leukoplakia differentially methylated genes. Four genes overlapped the 62 cancer/normal and the 168 leukoplakia/normal differentially methylated genes. (FIG. 2d) In addition, 92 potential tumor suppressor genes were hypermethylated in leukoplakia when compared to normal tissue and 168 potential proto-oncogenes were hypomethylated in leukoplakia when compared to normal tissue. Furthermore, 143 potential tumor suppressor genes were hypermethylated in cancer when compared to leukoplakia tissue and 47 potential proto-oncogenes were hypomethylated in leukoplakia when compared to normal tissue. (FIG. 2e)

Figure 2F:
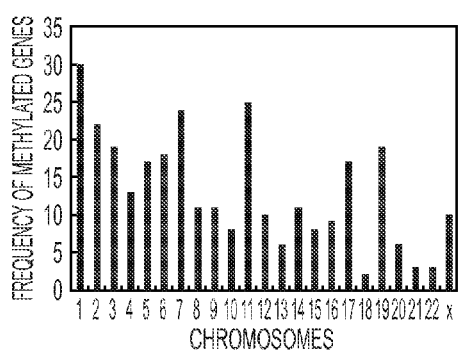
Figure 2G:
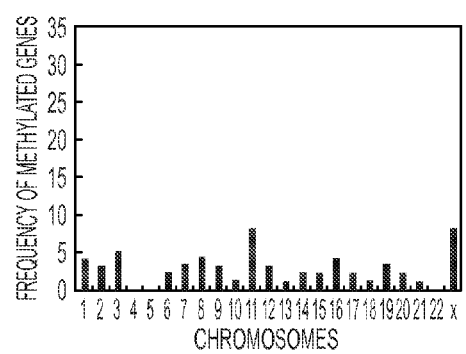

We then examined the chromosomal distribution of hypermethylated (FIG. 2f) and hypomethylated (FIG. 2g) genes in OSCC. There is a non-stochastic distribution for hypermethylation and hypomethylation events, which may be a reflection of both, driving oncogenic transformative events and phenotypic changes resultant from the oncogenic transformation. Most of the 301 hypermethylated genes are clustered from chromosome 1 to chromosome 11, while the majority of the 62 hypomethylated genes are clustered between chromosome 8 and chromosome 19.

EXAMPLE 3

Gene Ontology and Ingenuity Pathway Analysis of Hypermethylated Genes

The 301 hypermethylated differentially genes were analyzed for their biological significance using Geneontology (Spotfire®) and Ingenuity Pathway Analysis (IPA®). The differentially hypermethylated genes were found to be associated with pathways intimately related to oncogenic transformation: cell adhesion; cell proliferation; growth regulation; and cell death. ($p<0.05$)

The top associated network functions in IPA shown in are pathways directly related to tumorigenesis: cell signaling and interaction, nucleic acid metabolism, DNA replication, recombination and repair, cellular assembly organization, function and maintenance.

EXAMPLE 4

Analysis of Correlation of Promoter Hypermethylation with Gene Expression

Figure 3A:
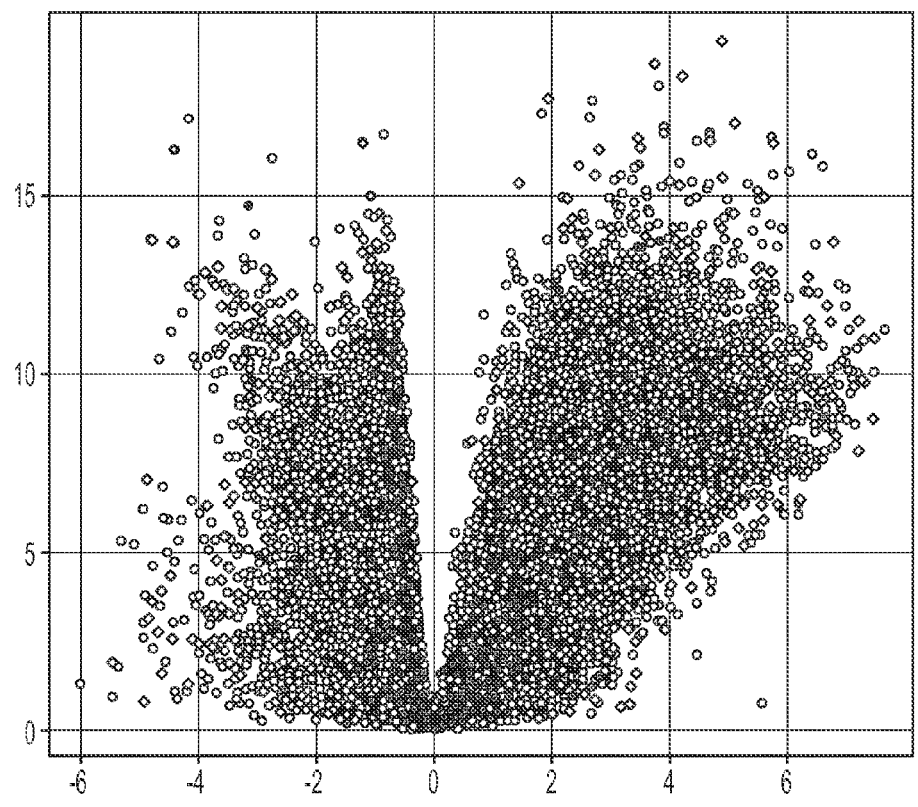
FIGS. 3A-3B.
Figure 3B:
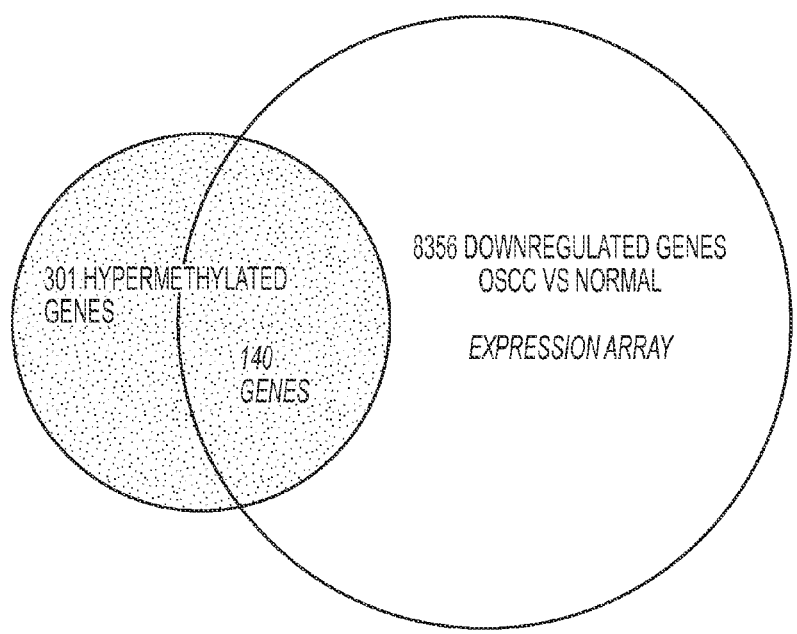

From the list of 301 hypermethylated genes in cancer we were able to find expression values for 275 of them in the expression arrays selected for methylation-transcriptional silencing analysis, 140 of which were downregulated. A volcano plot illustrating the correlation between the expression array results and our list of hypermethylated and hypomethylated genes is shown in FIG. 3A. A Venn diagram showing the relationship of down regulated genes in the expression array to the hypermethylated gene list is depicted in FIG. 3B.

EXAMPLE 5

Comparison to Existing Databases of Known Methylation Events in Cancer

We generated a list of genes that have been previously shown to be hypermethylated in OSCC/HNSCC and in other tumor tissues.

EXAMPLE 6

Target Gene Selection

Using multiple selection criteria we choose eight genes to validate on OSCC and normal oral mucosa tissue samples. The eight genes were among the 140 hypermethylated genes identified in the Discovery Screen that were also downregulated in the public expression database we examined for OSCC. Four of those genes (EDNRB, HOXA9, GATA4, and NID2) were identified as hypermethylated in non-OSCC/HNSCC tumor tissues in a Pubmed search [36-40]. Another four genes (MCAM, KIF1A, DCC, CALCA) were also found to be hypermethylated in existing databases of known methylation events in cancer [17, 18, 41]. Hypermethylation of EDNRB, KIF1A, and DCC has been previously shown to be associated with HNSCC histology. We thus chose these genes as benchmarks against which we could evaluate our genomic approach. CALCA, HOXA9, GATA4, and NID2 had never been shown to be hypermethylated in OSCC.

EXAMPLE 7

Promoter Methylation Association with Oral Cavity Malignancy

Figure 4:
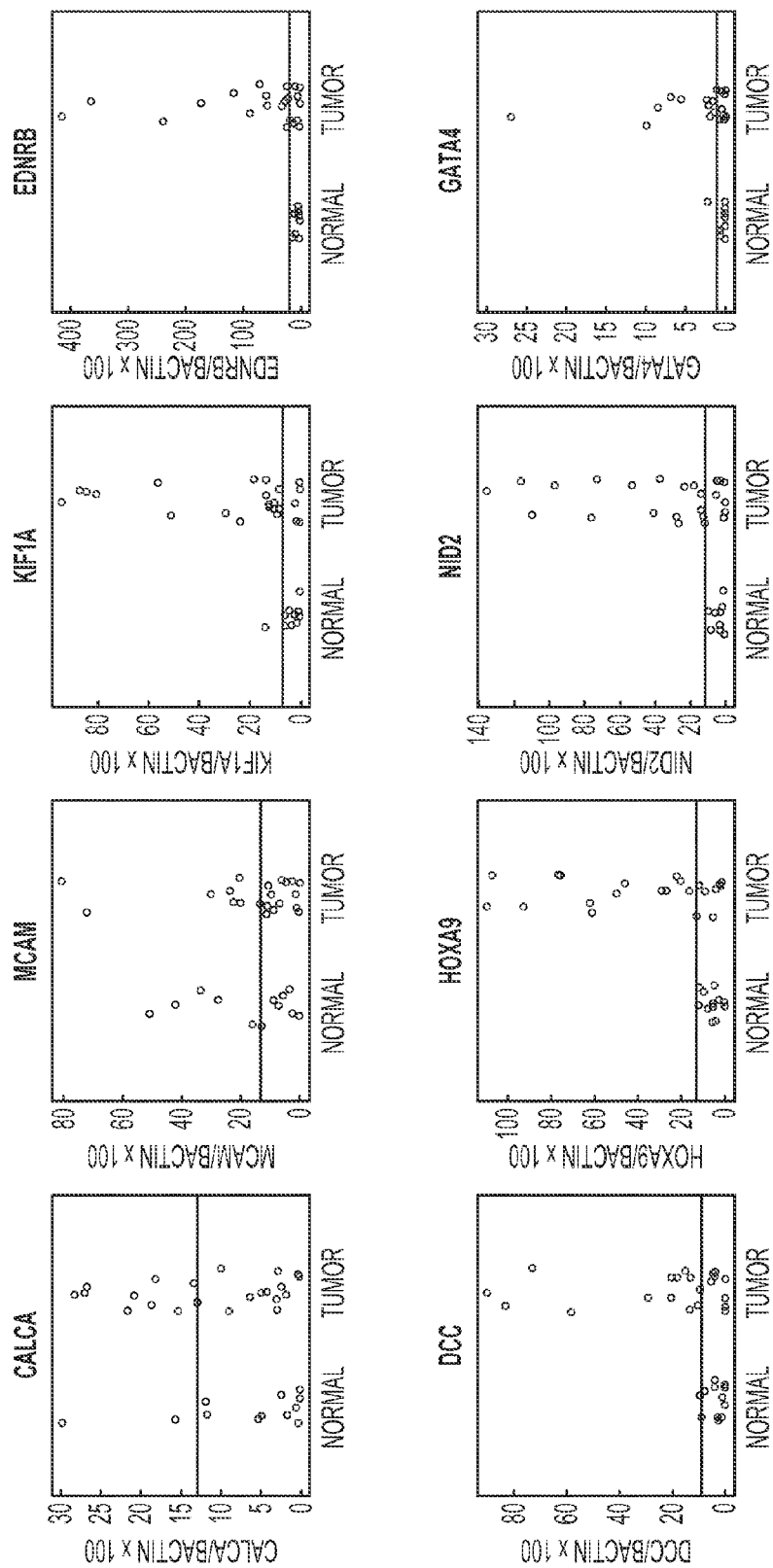
FIG. 4 provides scatterplots of quantitative MSP analysis of candidate genes promoters in the Discovery screen cohort, which consisted of 24 OSCC samples and 12 normal oral cavity mucosa tissues. The relative level of methylated DNA for each gene in each sample was determined as a ratio of MSP for the amplified gene to ACTB and then multiplied by 100 [(average value of duplicates of gene of interest/average value of duplicates of ACTB)×100] for EDNRB, HOXA9, GATA4, NID2, MCAM, KIF1A, GATA4, DCC, CALCA. The horizontal line denotes cutoff value.

Differential promoter methylation status was confirmed with qMSP in the Discovery screen. The Discovery screen cohort consisted of 24 OSCC samples and 12 normal oral cavity mucosa tissues obtained from the Madrid OSCC study. Six out of the eight genes, EDNRB, HOXA9, GATA4, NID2, KIF1A, DCC show differential methylation between cases and controls (FIG. 4). The promoter methylation status of the remainder two genes, CALCA and MCAM, however did not seem to differ between tumor tissue and normal mucosa.

Promoter methylation of KIF1A (κ=0.64), HOXA9 (κ=0.60), NID2 (κ=0.60), and EDNRB (κ=0.60) had a moderate to substantial agreement with clinical diagnosis in the Discovery screen. The four of them also had a percentage agreement equal to or greater than 79% (Table 1).

TABLE 1

Kappa statistic (k) of inter-classification agreement, 95% confidence intervals, and agreement percentage between classification of samples by promoter methylation of EDNRB, HOXA9, GATA4, NID2, _MCAM, KIF1A, DCC, CALCA and by clinical diagnosis (Discovery Screen - n = 36) and by histology (Prevalence Screen - n = 92).

| Variable | κ (95% CI) | Percentage agreement (%) |
|---|---|---|
| | Kappa coefficient | |
| | Discovery Screen | |
| HOXA9 | 0.60 (0.36, 0.84) | 79 |
| NID2 | 0.60 (0.36, 0.84) | 80 |
| GATA4 | 0.37 (0.09, 0.65) | 67 |
| KIF1A | 0.64 (0.39, 0.89) | 82 |
| EDNRB | 0.60 (0.36, 0.84) | 79 |
| DCC | 0.44 (0.18, 0.70) | 71 |
| MCAM | −0.12 (−0.42, 0.18) | 41 |
| CALCA | 0.24 (−0.02, 0.51) | 59 |
| | Prevalence Screen | |
| HOXA9 | 0.82 (0.70, 0.94) | 91 |
| NID2 | 0.80 (0.68, 0.92) | 90 |

Sensitivity, specificity, AUC, and methylation cut-off values for each of the genes evaluated in the Discovery Screen are shown in Table 2. Of the four candidate genes that had an AUC value equal to or higher than 0.75, only NID2 and HOXA9 had 100% specificity and sensitivity higher than 70%. We selected these two genes for further testing with the Prevalence Screen.

TABLE 2

Predictive accuracy of EDNRB, HOXA9, GATA4, NID2, _MCAM, KIF1A, DCC, CALCA with oral squamous cell carcinoma. Discovery Screen (n = 36); Prevalence Screen (n = 92)

| Predictor | Sensitivity % | Specificity % | AUC | Methylation Cutoff value |
|---|---|---|---|---|
| | Discovery Screen | | | |
| HOXA9 | 68 | 100 | 0.81 | 13.11 |
| NID2 | 71 | 100 | 0.79 | 11.48 |
| GATA4 | 57 | 89 | 0.72 | 0.96 |
| KIF1A | 77 | 92 | 0.79 | 7.14 |
| EDNRB | 68 | 100 | 0.83 | 17.42 |
| DCC | 55 | 92 | 0.74 | 9.04 |
| MCAM | 36 | 58 | 0.45 | 13.44 |
| CALCA | 46 | 83 | 0.67 | 12.85 |
| | Prevalence Screen | | | |
| HOXA9 | 85 | 97 | 0.91 | 13.11 |
| NID2 | 87 | 95 | 0.92 | 11.48 |
| HOXA9 and NID2 | 94 | 97 | 0.97 | * |

*Classified positive (+) if predicted probability for positive outcome (tumor) >= than 0.5

EXAMPLE 8

Prevalence Screen

Figure 5A:
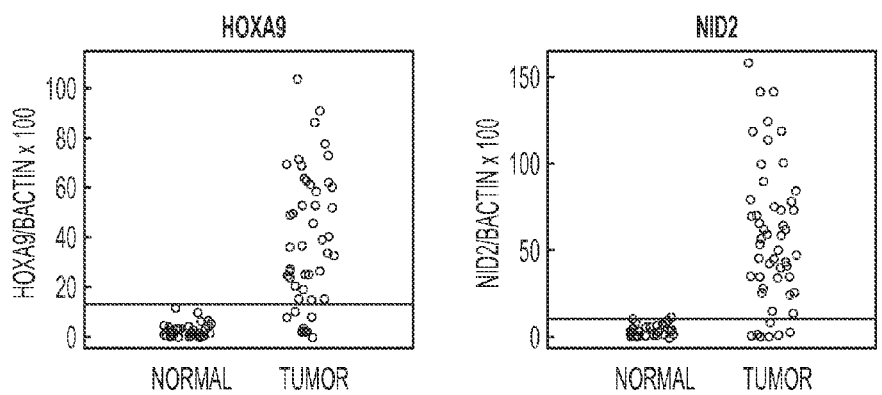
FIGS. 5A-5B.

We examined HOXA9 and NID2 promoter methylation status in 55 HNSCC tumor tissue samples and 37 normal tissue samples obtained from uvulopharyngopalatoplasty (UPPP) procedures performed in non-cancer patients. Minimal or no promoter methylation of HOXA9 and NID2 was observed in the normal oral cavity mucosa samples, while varying degrees of hypermethylation were present in the OSCC samples (FIG. 5A).

Figure 5B:
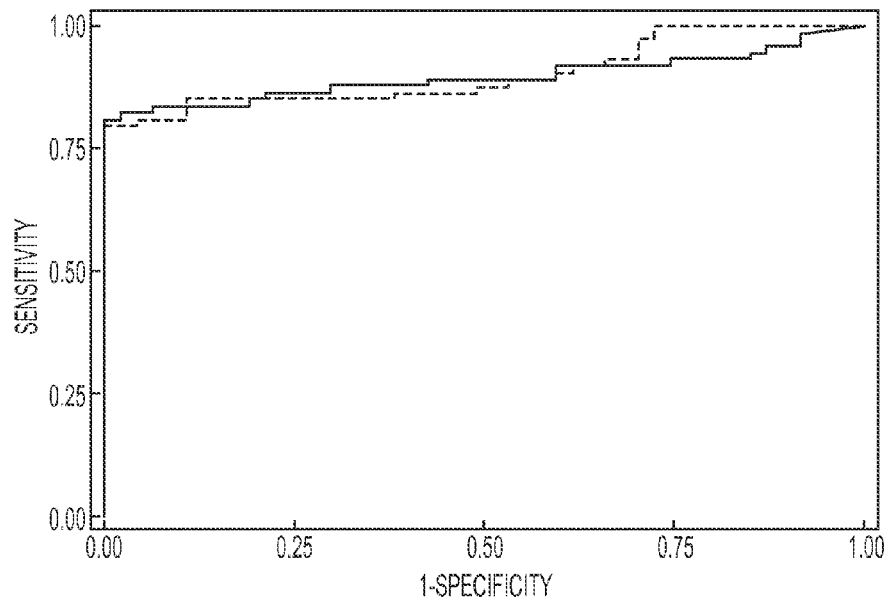

HOXA9 (κ=0.82; 95% CI, 0.70, 0.94) and NID2 (κ=0.80; 95% CI, 0.68, 0.92) had an almost perfect agreement with histologic diagnosis in the Prevalence Screen (Table 1). ROC analyses using the cut-off values optimized for the Discovery screen revealed that HOXA9 had 85% sensitivity, 97% specificity and a 0.95 AUC. NID2 had 87% sensitivity, 95% specificity and a 0.91 AUC (FIG. 5B). A HOXA9 and NID2 gene panel had 94% sensitivity, 97% specificity and a 0.97 AUC (Table 2)

EXAMPLE 9

Diagnostic Panel in Saliva—Oral and Oropharyngeal Squamous Cell Carcinoma

To test the feasibility of creating a diagnostic panel in saliva we examined the promoter methylation status of HOXA2 and NID2 in saliva samples from 16 patients with OSCC, 16 patients with oropharyngeal squamous cell carcinoma (OP-SCC) and saliva samples from 19 non-cancer patients. Promoter methylation of NID2 (κ=0.55) and HOXA9 (κ=0.52) had a moderate agreement with histologic diagnosis. (Table 3)

TABLE 3

Kappa statistic (k) of inter-classification agreement, 95% confidence intervals, and agreement percentage between sample classification by promoter methylation of HOXA9 and NID2 and by histology on head and neck cancer saliva samples. (n = 51)

| Variable | κ (95% CI) | Percentage agreement (%) |
|---|---|---|
| | Kappa coefficient | |
| | Oral and oropharyngeal cancer | |
| HOXA9 | 0.52 (−0.12, 0.42) | 59 |
| NID2 | 0.55 (−0.18, 0.37) | 59 |
| | Oral cancer | |
| HOXA9 | 0.21 (−0.11, 0.52) | 60 |
| NID2 | 0.23 (−0.03, 0.49) | 60 |

ROC analyses of the Prevalence Screen samples using the methylation cut-off values optimized for the Discovery Screen revealed that HOXA9 had a sensitivity of 63%, a specificity of 53% and an AUC of 0.65. NID2 had a sensitivity of 72%, a specificity of 21% and an AUC of 0.57. (Table 4)

TABLE 4

Predictive accuracy of HOXA9 and NID2 on head and neck cancer saliva samples. (n = 51)

| Predictor | Sensitivity % | Specificity % | AUC | Methylation Cutoff value |
|---|---|---|---|---|
| | Oral and oropharyngeal cancer (n = 51) | | | |
| HOXA9 | 63 | 53 | 0.65 | 13.11 |
| NID2 | 72 | 21 | 0.57 | 11.48 |
| | Oral cancer (n = 35) | | | |
| HOXA9 | 75 | 53 | 0.75 | 13.11 |
| NID2 | 87 | 21 | 0.73 | 11.48 |
| HOXA9 and NID2 | 50 | 90 | 0.75 | * |

*Classified positive (+) if predicted probability for positive outcome (tumor) >= than 0.5

EXAMPLE 10

Diagnostic Panel in Saliva—Oral Squamous Cell Carcinoma

We then examined the use of promoter methylation status of HOXA2 and NID2 for cancer detection in saliva samples from 16 patients with OSCC and saliva samples from 19 non-cancer patients. Promoter methylation of NID2 (κ=0.23) and HOXA9 (κ=0.21) had a fair agreement with histologic diagnosis. (Table 3). ROC analyses using the cut-off values optimized for the discovery screen revealed that HOXA9 had a sensitivity of 75%, a specificity of 53% and an AUC of 0.75. NID2 had a sensitivity of 87%, a specificity of 21% and an AUC of 0.73. A panel of HOXA9 and NID2 had a sensitivity of 50%, a specificity of 90% and an AUC of 0.77. (Table 4)

The numbers of cancer/non-cancer patients, and unmethylated/methylated samples in each category for the Discovery, Prevalence and Saliva screens are described in. The table also describes the thresholds of promoter methylation levels (cut-off levels).

REFERENCES

The disclosure of each reference cited is expressly incorporated herein.

1. Warnakulasuriya, S., *Global epidemiology of oral and oropharyngeal cancer*. Oral Oncol, 2009. 45(4-5): p. 309-16.
2. Yako-Suketomo, H. and T. Matsuda, *Comparison of time trends in lip, oral cavity and pharynx cancer mortality (1990-2006) between countries based on the WHO mortality database*. Jpn J Clin Oncol. 40(11): p. 1118-9.
3. Goldstein, B. Y., et al., *Alcohol consumption and cancers of the oral cavity and pharynx from 1988 to 2009: an update*. Eur J Cancer Prev. 19(6): p. 431-65.
4. Zini, A., R. Czerninski, and H. D. Sgan-Cohen, *Oral cancer over four decades: epidemiology, trends, histology, and survival by anatomical sites*. J Oral Pathol Med. 39(4): p. 299-305.
5. Hashibe, M., et al., *Interaction between tobacco and alcohol use and the risk of head and neck cancer: pooled analysis in the International Head and Neck Cancer Epidemiology Consortium*. Cancer Epidemiol Biomarkers Prev, 2009. 18(2): p. 541-50.
6. Kreeft, A., et al., *The surgical dilemma of 'functional inoperability' in oral and oropharyngeal cancer: current consensus on operability regard to functional results*. Clin Otolaryngol, 2009. 34(2): p. 140-6.
7. Glazer, C. A., et al., *Applying the molecular biology and epigenetics of head and neck cancer in everyday clinical practice*. Oral Oncol, 2009. 45(4-5): p. 440-6.
8. Kagan, J., et al., *Towards Clinical Application of Methylated DNA Sequences as Cancer Biomarkers: A Joint NCI's EDRN and NIST Workshop on Standards, Methods, Assays, Reagents and Tools*. Cancer Res, 2007. 67(10): p. 4545-9.
9. Hudson, T. J., et al., *International network of cancer genome projects*. Nature. 464(7291): p. 993-8.
10. Ha, P. K. and J. A. Califano, *Promoter methylation and inactivation of tumour-suppressor genes in oral squamous-cell carcinoma*. Lancet Oncol, 2006. 7(1): p. 77-82.
11. Smith, I. M., et al., *Coordinated activation of candidate proto-oncogenes and cancer testes antigens via promoter demethylation in head and neck cancer and lung cancer*. PLoS One, 2009. 4(3): p. e4961.
12. Glazer, C. A., et al., *Integrative discovery of epigenetically derepressed cancer testis antigens in NSCLC*. PLoS One, 2009. 4(12): p. e8189.
13. Rosas, S. L., et al., *Promoter hypermethylation patterns of p16, O6-methylguanine-DNA-methyltransferase, and death-associated protein kinase in tumors and saliva of head and neck cancer patients*. Cancer Res, 2001. 61(3): p. 939-42.
14. Shaw, R., *The epigenetics of oral cancer*. Int J Oral Maxillofac Surg, 2006. 35(2): p. 101-8.
15. Carvalho, A. L., et al., *Evaluation of promoter hypermethylation detection in body fluids as a screening/diagnosis tool for head and neck squamous cell carcinoma*, Clin Cancer Res, 2008. 14(1): p. 97-107.
16. Chang, X., et al., *Identification of hypermethylated genes associated with cisplatin resistance in human cancers*. Cancer Res. 70(7): p. 2870-9.
17. Demokan, S., et al., *KIF1A and EDNRB are differentially methylated primary HNSCC and salivary rinses*. Int J Cancer. 127(10): p. 2351-9.
18. Pattani, K. M., et al., *Endothelin receptor type B gene promoter hypermethylation in salivary rinses is independently associated with risk of oral cavity cancer and premalignancy*. Cancer Prev Res (Phila). 3(9): p. 1093-103.
19. Righini, C. A., et al., *Tumor-specific methylation in saliva: a promising biomarker for early detection of head and neck cancer recurrence*. Clin Cancer Res, 2007. 13(4): p. 1179-85.
20. Viet, C. T. and B. L. Schmidt, *Methylation array analysis of preoperative and postoperative saliva DNA in oral cancer patients*. Cancer Epidemiol Biomarkers Prev, 2008. 17(12): p. 3603-11.
21. Yamashita, K., et al., *Genetics supersedes epigenetics in colon cancer phenotype*. Cancer Cell, 2003. 4(2): p. 121-31.
22. Marsit, C. J., et al., *Epigenetic profiling reveals etiologically distinct patterns of DNA methylation in head and neck squamous cell carcinoma*. Carcinogenesis, 2009. 30(3): p. 416-22.
23. Smith, I. M., et al., *DNA global hypomethylation in squamous cell head and neck cancer associated with smoking, alcohol consumption and stage*. Int J Cancer, 2007. 121(8): p. 1724-8.
24. Hawkins, R. D., G. C. Hon, and B. Ren, *Next-generation genomics: an integrative approach*. Nat Rev Genet. 11(7): p. 476-486.
25. Khachatryan, V., et al., *First measurement of Bose-Einstein correlations in proton-proton collisions at radicals=0.9 and 2.36 TeV at the LHC*. Phys Rev Lett. 105(3): p. 032001.
26. Hawkins, R. D., et al., *Distinct epigenomic landscapes of pluripotent and lineage-committed human cells*. Cell Stem Cell. 6(5): p. 479-91.
27, Pepe, M. S., et al., *Phases of biomarker development for early detection of cancer*. J Nat'l Cancer Inst, 2001. 93(14): p. 1054-61.
28, Srivastava, S., *Cancer biomarker discovery and development in gastrointestinal cancers: early detection research network-a collaborative approach*. Gastrointest Cancer Res, 2007. 1(4 Suppl 2): p. 560-3.
29. Moreno-Lopez, L. A., et al., *Risk of oral cancer associated with tobacco smoking, alcohol consumption and oral hygiene: a case-control study in Madrid, Spain*. Oral Oncol, 2000. 36(2): p. 170-4.
30. Varela-Lema, L., et al., *Tobacco consumption and oral and pharyngeal cancer in a Spanish male population*. Cancer Lett. 288(1): p. 28-35.
31. Storey, J. D. and R. Tibshirani, *Statistical significance for genomewide studies*. Proc Natl Acad Sci USA, 2003. 100 (16): p. 9440-5.

32. Fang, Y. C., H. C. Huang, and H. F. Juan, *MeInfoText: associated gene methylation and cancer information from text mining.* BMC Bioinformatics, 2008. 9: p. 22.
33. He, X., et al., *MethylCancer: the database of human DNA methylation and cancer.* Nucleic Acids Res, 2008. 36(Database issue): p. D836-41.
34. Sticht, C., et al., *Activation of MAP kinase signaling through ERK5 but not ERK1 expression is associated with lymph node metastases in oral squamous cell carcinoma (OSCC).* Neoplasia, 2008. 10(5): p. 462-70.
35. Hoque, M. O., et al., *Quantitation of promoter methylation of multiple genes in urine DNA and bladder cancer detection.* J Natl Cancer Inst, 2006. 98(14): p. 996-1004.
36. Ulazzi, L., et al., *Nidogen 1 and 2 gene promoters are aberrantly methylated in human gastrointestinal cancer.* Mol Cancer, 2007. 6: p. 17.
37. Renard, I., et al., *Identification and validation of the methylated TWIST1 and NID2 genes through real-time methylation-specific polymerase chain reaction assays for the noninvasive detection of primary bladder cancer in urine samples.* Eur Urol. 58(1): p. 96-104.
38. Gilbert, P. M., et al., *HOXA9 regulates BRCA1 expression to modulate human breast tumor phenotype.* J Clin Invest. 120(5): p. 1535-50.
39. Ahlquist, T., et al., *Gene methylation profiles of normal mucosa, and benign and malignant colorectal tumors identify early onset markers.* Mol Cancer, 2008. 7: p. 94.
40. Hellebrekers, D. M., et al., *GATA4 and GATA5 are potential tumor suppressors and biomarkers in colorectal cancer.* Clin Cancer Res, 2009. 15(12): p. 3990-7.
41. Liu, J. W., et al., *Hypermethylation of MCAM gene is associated with advanced tumor stage in prostate cancer.* Prostate, 2008. 68(4): p. 418-26.
42. Weinstein, I. B. and A. Joe, *Oncogene addiction.* Cancer Res, 2008. 68(9): p. 3077-80; discussion 3080.
43. Weinstein, I. B., *Cancer. Addiction to oncogenes—the Achilles heal of cancer.* Science, 2002. 297(5578): p. 63-4.
44. Tonon, G., *From oncogene to network addiction: the new frontier of cancer genomics and therapeutics.* Future Oncol, 2008. 4(4): p. 569-77.
45. Terry, M. B., et al., *Polymorphism in the DNA repair gene XPD, polycyclic aromatic hydrocarbon-DNA adducts, cigarette smoking, and breast cancer risk.* Cancer Epidemiol Biomarkers Prev, 2004. 13(12): p, 2053-8,
46. Pepe, M. S., et al., *Integrating the predictiveness of a marker with its performance as a classifier.* Am J Epidemiol, 2008. 167(3): p, 362-8.

We claim:

1. A method for identifying oral squamous cell cancer (OSCC) in a human patient comprising:
   a) obtaining nucleic acid from a test sample taken from the oral cavity mucosal tissues of the patient, wherein the test sample is from a specimen selected from the group consisting of a tissue specimen, a biopsy specimen, a surgical specimen, saliva, and a cytological specimen;
   b) obtaining nucleic acid from an oral mucosal non-neoplastic reference sample wherein the reference sample is from a specimen selected from the group consisting of a tissue specimen, a biopsy specimen, a surgical specimen, saliva, and a cytological specimen;
   c) performing bisulfite modification to the nucleic acid in steps a) and b);
   d) performing quantitative methylation specific PCR (QMSP) on the bisulfite modified nucleic acid from step c) using PCR primers and probes specific for the promoter region of the HOXA9 and NID2 genes, wherein the primers and probes are SEQ ID NOS:10-15;
   e) determining the promoter methylation level of the promoter regions HOXA9 and NID2 in the test sample and the reference sample;
   f) comparing the level of promoter methylation of HOXA9 and NID2 from the test sample of the patient, to the level of promoter methylation of HOXA9 and NID2 in the reference sample;
   g) identifying said patient as having OSCC when the level of methylation of the promoter regions of HOXA9 and NID2 are increased relative to the level of methylation of the promoter regions of HOXA9 and NID2 in the reference sample.

2. The method of claim 1 wherein the test sample from the patient contains oral squamous cells or nucleic acids from oral squamous cells.

3. The method of claim 1, further comprising:
   h) performing RT-PCR on a portion of the nucleic acid from the test sample in step a) and the reference sample in step b) using PCR primers specific for HOXA9 and NID2;
   i) determining the mRNA expression level of HOXA9 and NID2 in the test sample and the reference sample;
   j) comparing the mRNA expression level of HOXA9 and NID2 in the test sample and the reference sample; and
   k) identifying said patient as having OSCC when the level of methylation of the promoter regions of HOXA9 and NID2 are increased relative to the level of methylation of the promoter regions of HOXA9 and NID2 in the reference sample and the level of mRNA expression of HOXA9 and NID2 in the test sample is decreased relative to the level of mRNA expression of HOXA9 and NID2 in the reference sample.

4. The method of claim 1 further comprising, at step d), performing quantitative methylation specific PCR (QMSP) on bisulfite modified nucleic acid from step c) using PCR primers and probes specific for the promoter region of at least one or more additional genes of interest, wherein the additional genes of interest are selected from the group consisting of EDNRB, KIF1a, GATA4, and DCC, and the primers and probes specific for the promoter region of the genes of interest are selected from the group consisting of SEQ ID) NOS:4-9, and 22-27.

5. The method of claim 4, wherein the at least one or more additional genes of interest is two more additional genes of interest.

6. The method of claim 4, wherein the at least one or more additional genes of interest is three more additional genes of interest.

7. The method of claim 4, wherein the at least one or more additional genes of interest is four more additional genes of interest.

\* \* \* \* \*